United States Patent [19]
Lehner et al.

[11] Patent Number: 6,024,958
[45] Date of Patent: Feb. 15, 2000

[54] **POLYPEPTIDE FRAGMENTS CAPABLE OF COMPETITION WITH *STREPTOCOCCUS MUTANS* ANTIGEN I/II**

[75] Inventors: Thomas Lehner; Charles Kelly, both of London, United Kingdom

[73] Assignee: The Council of Governors of the United Medical & Dental School of Guy's & St. Thomas's Hospitals, United Kingdom

[21] Appl. No.: 08/894,017

[22] PCT Filed: Jan. 31, 1996

[86] PCT No.: PCT/GB96/00207

§ 371 Date: Oct. 20, 1997

§ 102(e) Date: Oct. 20, 1997

[87] PCT Pub. No.: WO96/23886

PCT Pub. Date: Aug. 8, 1996

[30] Foreign Application Priority Data

Jan. 31, 1995 [GB] United Kingdom ............. 9501826

[51] Int. Cl.[7] .................. A61K 39/00; A61K 39/02; A61K 39/09; C07K 5/00
[52] U.S. Cl. ............................ 424/190.1; 424/185.1; 424/244.1; 530/324; 530/325; 530/326; 530/327; 530/328; 530/329; 530/350
[58] Field of Search ............................ 530/350, 324, 530/325, 326, 327, 328, 329; 424/181.1, 190.1, 244.1

[56] References Cited

U.S. PATENT DOCUMENTS 5,258,368  11/1993  Lewicki et al. .

FOREIGN PATENT DOCUMENTS

| 116472 | 2/1984 | European Pat. Off. . |
| 280576 | 2/1988 | European Pat. Off. . |
| 2060647 | 5/1981 | United Kingdom . |

OTHER PUBLICATIONS

Moisset et al: Infection and Immunity, vol. 62 No. 1, Jan. 1994, pp. 183–193.
Munro et al.: Infection and Immunity, vol 61 No. 11, Nov. 1993, pp. 4590–4598.
Munro et al.: J. Dent. Res. 71 (IADR Abstracts); 1992, 7235, Abstact 1753.
Kelly et al.: J. Dent. Res. 71 (IADR Abstracts); 1992, 517, Abstract 17.
Kelly et al.: Infection and Immunity, vol. 63 No. 9, Sep. 1995, pp. 3649–3658.
Simitsek et al.: J. Exp. Med. 4181, Jun. 1995, pp. 1957–1963.
Watts and Lanzavecchia: J. Exp. Med. 4178, Oct. 1993, pp. 1459–1463.
Barnett et al.: Eur. J. Immunol. 19 (1989) pp. 515–521.
Adorini et al.: The Jounal of Experimental Medicine, vol. 168, Dec. 1988, pp. 2091–2104.
Smith–Gill et al.: The Journal of Immunology, vol. 125 No. 1, Jan. 1982, pp. 314–322.
Sheriff et al.: Proc. Natl. Acad. Sci., USA 84 (1987) pp. 8075–8079.
Charles et al.: Eur. J. Immunol., 1991, 21, pp. 1147–1153.
Emsly et al.: Nature 4381, May 1986, pp. 90–92.
Jacobs et al.: J. Med. Microbiol., vol. 43 (1995), pp. 422–429.
Neurath et al.: Cell, vol. 46, pp. 429–436, Aug. 1$^{st}$, 1986.
Neutath et al.: Exp. Med 4175, Feb. 1992, pp. 461–469.
Greenstein et al.: The Journal of Immunology, vol. 148, pp. 3970–3977, (1992).
Steward et al.: Vaccine vol. 11, issue 14, 1993, pp. 1405–1414.
Brady et al.: Infection and Immunity, vol. 16, No. 3, Mar. 1992, pp. 1008–1017.
Lehner et al.: "T–Ce;; and B–Ce;; T–Cell and B–Cell Eptiope mapping and construction of peptide vaccines"; Cjhapter 24 in "Molecular Pathogen esis of Periodontal Disease", edited by Robert Geneco et al., © 1994 American Sociey for Micobiology.
Abstracts 234 (Kendal et al.), 235 (Todryk et al.) and 238 (Ma et al.); J. Dent Res., Apr. 1994, vol 73, No. 4.
Kelly et al.: Immunology, vol. 87, pp. 55–63, (1995).
Lazar et al. Mol. Cell. Biology 8(3):1247–52, Mar. 1988.
Burgess et al. J.Cell Biology 111:2129–38, Nov. 1990.
Solgaller et al. Caner Immunol. Immunother. 105–116, 1994.

*Primary Examiner*—Anthony C. Caputa
*Assistant Examiner*—Mark Navarro
*Attorney, Agent, or Firm*—Morrison & Foerster, LLP

[57] ABSTRACT

Defined peptide subunits of *Streptococcus mutans* antigen I/II are useful as agents to prevent and treat dental caries either by eliciting an immunological response or by preventing adhesion of *S. mutans* to the tooth.

31 Claims, 7 Drawing Sheets

6,024,958

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
       (A) LENGTH: 190 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Thr Glu Lys Pro Leu Glu Pro Ala Pro Val Glu Pro Ser Tyr Glu Ala
 1               5                  10                  15

Glu Pro Thr Pro Pro Thr Pro Thr Pro Asp Gln Pro Glu Pro Asn Lys

```
                    20                  25                  30
Pro Val Glu Pro Thr Tyr Glu Val Ile Pro Thr Pro Pro Thr Asp Pro
        35                  40                  45
Val Tyr Gln Asp Leu Pro Thr Pro Pro Ser Ile Pro Thr Val His Phe
 50                  55                  60
His Tyr Phe Lys Leu Ala Val Gln Pro Gln Val Asn Lys Glu Ile Arg
 65                  70                  75                  80
Asn Asn Asn Asp Val Asn Ile Asp Arg Thr Leu Val Ala Lys Gln Ser
                85                  90                  95
Val Val Lys Phe Gln Leu Lys Thr Ala Asp Leu Pro Ala Gly Arg Asp
                100                 105                 110
Glu Thr Thr Ser Phe Val Leu Val Asp Pro Leu Pro Ser Gly Tyr Gln
                115                 120                 125
Phe Asn Pro Glu Ala Thr Lys Ala Ala Ser Pro Gly Phe Asp Val Ala
130                 135                 140
Tyr Asp Asn Ala Thr Asn Thr Val Thr Phe Lys Ala Thr Ala Ala Thr
145                 150                 155                 160
Leu Ala Thr Phe Asn Ala Asp Leu Thr Lys Ser Val Ala Thr Ile Tyr
                165                 170                 175
Pro Thr Val Val Gly Gln Val Leu Asn Asp Gly Ala Thr Tyr
                180                 185                 190

(2) INFORMATION FOR SEQ ID NO:2:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Asn Asn Asn Asp Val Asn Ile Asp Arg Thr Leu Val Ala Lys Gln Ser
 1                   5                  10                  15
Val Val Lys Phe Gln Leu Lys Thr Ala Asp Leu Pro Ala Gly Arg Asp
                20                  25                  30
Glu Thr Thr Ser Phe Val Leu Val
                35                  40

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Leu Ala Thr Phe Asn Ala Asp Leu Thr Lys Ser Val Ala Thr Ile Tyr
 1                   5                  10                  15
Pro Thr Val Val
                20

(2) INFORMATION FOR SEQ ID NO:4:

(i) SEQUENCE CHARACTERISTICS:
        (A) LENGTH: 110 amino acids
        (B) TYPE: amino acid
```

(C) STRANDEDNESS: single
              (D) TOPOLOGY: linear (ii) MOLECULE TYPE: peptide (xi) SEQUENCE DESCRIPTION: SEQ ID NO:4:

Asn Asn Asn Asp Val Asn Ile Asp Arg Thr Leu Val Ala Lys Gln Ser
1               5                   10                  15

Val Val Lys Phe Gln Leu Lys Thr Ala Asp Leu Pro Ala Gly Arg Asp
            20                  25                  30

Glu Thr Thr Ser Phe Val Leu Val Asp Pro Leu Pro Ser Gly Tyr Gln
        35                  40                  45

Phe Asn Pro Glu Ala Thr Lys Ala Ala Ser Pro Gly Phe Asp Val Ala
    50                  55                  60

Tyr Asp Asn Ala Thr Asn Thr Val Thr Phe Lys Ala Thr Ala Ala Thr
65                  70                  75                  80

Leu Ala Thr Phe Asn Ala Asp Leu Thr Lys Ser Val Ala Thr Ile Tyr
                85                  90                  95

Pro Thr Val Val Gly Gln Val Leu Asn Asp Gly Ala Thr Tyr
            100                 105                 110

(2) INFORMATION FOR SEQ ID NO:5:

(i) SEQUENCE CHARACTERISTICS:
              (A) LENGTH: 80 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:5:

Thr Glu Lys Pro Leu Glu Pro Ala Pro Val Glu Pro Ser Tyr Glu Ala
1               5                   10                  15

Glu Pro Thr Pro Pro Thr Pro Thr Pro Asp Gln Pro Glu Pro Asn Lys
            20                  25                  30

Pro Val Glu Pro Thr Tyr Glu Val Ile Pro Thr Pro Thr Asp Pro
        35                  40                  45

Val Tyr Gln Asp Leu Pro Thr Pro Pro Ser Ile Pro Thr Val His Phe
    50                  55                  60

His Tyr Phe Lys Leu Ala Val Gln Pro Gln Val Asn Lys Glu Ile Arg
65                  70                  75                  80

(2) INFORMATION FOR SEQ ID NO:6:

(i) SEQUENCE CHARACTERISTICS:
              (A) LENGTH: 130 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:6:

Thr Glu Lys Pro Leu Glu Pro Ala Pro Val Glu Pro Ser Tyr Glu Ala
1               5                   10                  15

Glu Pro Thr Pro Pro Thr Pro Thr Pro Asp Gln Pro Glu Pro Asn Lys
            20                  25                  30

Pro Val Glu Pro Thr Tyr Glu Val Ile Pro Thr Pro Thr Asp Pro
        35                  40                  45

Val Tyr Gln Asp Leu Pro Thr Pro Pro Ser Ile Pro Thr Val His Phe

```
             50                  55                  60
His Tyr Phe Lys Leu Ala Val Gln Pro Gln Val Asn Lys Glu Ile Arg
 65                  70                  75                  80

Asn Asn Asn Asp Val Asn Ile Asp Arg Thr Leu Val Ala Lys Gln Ser
                 85                  90                  95

Val Val Lys Phe Gln Leu Lys Thr Ala Asp Leu Pro Ala Gly Arg Asp
            100                 105                 110

Glu Thr Thr Ser Phe Val Leu Val Asp Pro Leu Pro Ser Gly Tyr Gln
            115                 120                 125

Phe Asn
    130
```

(2) INFORMATION FOR SEQ ID NO:7:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Glu Thr Gly Lys Lys Pro Asn Ile Trp Tyr Ser Leu Asn Gly Lys Ile
  1               5                  10                  15

Arg Ala Val Asn Leu Pro Lys Val Thr Lys Glu Lys Pro Thr Pro Pro
                 20                  25                  30

Val Lys Pro Thr Ala Pro Thr Lys Pro Thr Tyr Glu Thr Glu Lys Pro
             35                  40                  45

Leu Lys Pro Ala
    50
```

(2) INFORMATION FOR SEQ ID NO:8:

(i) SEQUENCE CHARACTERISTICS:
        (A) LENGTH: 70 amino acids
        (B) TYPE: amino acid
        (C) STRANDEDNESS: single
        (D) TOPOLOGY: linear (xi) SEQUENCE DESCRIPTION: SEQ ID NO:8:

```
Gln Asp Leu Pro Thr Pro Pro Ser Ile Pro Thr Val His Phe His Tyr
  1               5                  10                  15

Phe Lys Leu Ala Val Gln Pro Gln Val Asn Lys Glu Ile Arg Asn Asn
                 20                  25                  30

Asn Asp Val Asn Ile Asp Arg Thr Leu Val Ala Lys Gln Ser Val Val
             35                  40                  45

Lys Phe Gln Leu Lys Thr Ala Asp Leu Pro Ala Gly Arg Asp Glu Thr
    50                  55                  60

Thr Ser Phe Val Leu Val
 65                  70
```

(2) INFORMATION FOR SEQ ID NO:9:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO:9:

Phe Gln Leu Lys Thr Ala Asp Leu Pro Ala Gly Arg Asp Glu Thr Thr
1               5                   10                  15

Ser Phe Val Leu Val
            20

(2) INFORMATION FOR SEQ ID NO:10:

(i) SEQUENCE CHARACTERISTICS:
        (A) LENGTH: 312 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Glu Thr Gly Lys Lys Pro Asn Ile Trp Tyr Ser Leu Asn Gly Lys Ile
1               5                   10                  15

Arg Ala Val Asn Leu Pro Lys Val Thr Lys Glu Lys Pro Thr Pro Pro
                20                  25                  30

Val Lys Pro Thr Ala Pro Thr Lys Pro Thr Tyr Glu Thr Glu Lys Pro
        35                  40                  45

Leu Lys Pro Ala Pro Val Ala Pro Asn Tyr Glu Lys Glu Pro Thr Pro
    50                  55                  60

Pro Thr Arg Thr Pro Asp Gln Ala Glu Pro Lys Lys Pro Thr Pro Pro
65                  70                  75                  80

Thr Tyr Glu Thr Glu Lys Pro Leu Glu Pro Ala Pro Val Glu Pro Ser
                85                  90                  95

Tyr Glu Ala Glu Pro Thr Pro Pro Thr Arg Thr Pro Asp Gln Ala Glu
                100                 105                 110

Pro Asn Lys Pro Thr Pro Pro Thr Tyr Glu Thr Glu Lys Pro Leu Glu
            115                 120                 125

Pro Ala Pro Val Glu Pro Ser Tyr Glu Ala Glu Pro Thr Pro Pro Thr
        130                 135                 140

Pro Thr Pro Asp Gln Pro Glu Pro Asn Lys Pro Val Glu Pro Thr Tyr
145                 150                 155                 160

Glu Val Ile Pro Thr Pro Pro Thr Asp Pro Val Tyr Gln Asp Leu Pro
                165                 170                 175

Thr Pro Pro Ser Ile Pro Thr Val His Phe His Tyr Phe Lys Leu Ala
            180                 185                 190

Val Gln Pro Gln Val Asn Lys Glu Ile Arg Asn Asn Asn Asp Val Asn
        195                 200                 205

Ile Asp Arg Thr Leu Val Ala Lys Gln Ser Val Val Lys Phe Gln Leu
    210                 215                 220

Lys Thr Ala Asp Leu Pro Ala Gly Arg Asp Glu Thr Thr Ser Phe Val
225                 230                 235                 240

Leu Val Asp Pro Leu Pro Ser Gly Tyr Gln Phe Asn Pro Glu Ala Thr
                245                 250                 255

Lys Ala Ala Ser Pro Gly Phe Asp Val Ala Tyr Asp Asn Ala Thr Asn
            260                 265                 270

Thr Val Thr Phe Lys Ala Thr Ala Thr Leu Ala Thr Phe Asn Ala
        275                 280                 285

Asp Leu Thr Lys Ser Val Ala Thr Ile Tyr Pro Thr Val Val Gly Gln
    290                 295                 300

Val Leu Asn Asp Gly Ala Thr Tyr

(2) INFORMATION FOR SEQ ID NO:11:

(i) SEQUENCE CHARACTERISTICS:
       (A) LENGTH: 30 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:11:

Gln Asp Leu Pro Thr Pro Pro Ser Ile Pro Thr Val His Phe His Tyr
 1               5                  10                  15

Phe Lys Leu Ala Val Gln Pro Gln Val Asn Lys Glu Ile Arg
             20                  25                  30

(2) INFORMATION FOR SEQ ID NO:12:

(i) SEQUENCE CHARACTERISTICS:
       (A) LENGTH: 570 base pairs
       (B) TYPE: nucleic acid
       (C) STRANDEDNESS: double
       (D) TOPOLOGY: linear (ii) MOLECULE TYPE: Genomic DNA (xi) SEQUENCE DESCRIPTION: SEQ ID NO:12:

```
ACAGAAAAGC CGTTGGAGCC AGCACCTGTT GAGCCAAGCT ATGAAGCAGA GCCAACGCCA      60
CCGACACCAA CACCAGATCA ACCAGAACCA AACAAACCTG TTGAGCCAAC TTATGAGGTT     120
ATTCCAACAC CGCCGACTGA TCCTGTTTAT CAAGATCTTC CAACACCTCC ATCTATACCA     180
ACTGTTCATT TCCATTACTT TAAACTAGCT GTTCAGCCGC AGGTTAACAA AGAAATTAGA     240
AACAATAACG ATGTTAATAT TGACAGAACT TTGGTGGCTA ACAATCTGT TGTTAAGTTC      300
CAGCTGAAGA CAGCAGATCT CCCTGCTGGA CGTGATGAAA CAACTTCCTT TGTCTTGGTA     360
GATCCCCTGC CATCTGGTTA TCAATTTAAT CCTGAAGCTA CAAAAGCTGC CAGCCCTGGC     420
TTTGATGTCG CTTATGATAA TGCAACTAAT ACAGTCACCT TCAAGGCAAC TGCAGCAACT     480
TTGGCTACGT TTAATGCTGA TTTGACTAAG TCAGTGGCAA CGATTTATCC AACAGTGGTC     540
GGACAAGTTC TTAATGATGG CGCAACTTAT                                     570
```

(2) INFORMATION FOR SEQ ID NO:13:

(i) SEQUENCE CHARACTERISTICS:
       (A) LENGTH: 120 base pairs
       (B) TYPE: nucleic acid
       (C) STRANDEDNESS: double
       (D) TOPOLOGY: linear (ii) MOLECULE TYPE: Genomic DNA (xi) SEQUENCE DESCRIPTION: SEQ ID NO:13:

```
AACAATAACG ATGTTAATAT TGACAGAACT TTGGTGGCTA ACAATCTGT TGTTAAGTTC       60
CAGCTGAAGA CAGCAGATCT CCCTGCTGGA CGTGATGAAA CAACTTCCTT TGTCTTGGTA    120
```

(2) INFORMATION FOR SEQ ID NO:14:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:14:

TTGGCTACGT TTAATGCTGA TTTGACTAAG TCAGTGGCAA CGATTTATCC AACAGTGGTC            60

(2) INFORMATION FOR SEQ ID NO:15:

(i) SEQUENCE CHARACTERISTICS:
            (A) LENGTH: 330 base pairs
            (B) TYPE: nucleic acid
            (C) STRANDEDNESS: double
            (D) TOPOLOGY: linear (ii) MOLECULE TYPE: Genomic DNA (xi) SEQUENCE DESCRIPTION: SEQ ID NO:15:

AACAATAACG ATGTTAATAT TGACAGAACT TTGGTGGCTA AACAATCTGT TGTTAAGTTC            60

CAGCTGAAGA CAGCAGATCT CCCTGCTGGA CGTGATGAAA CAACTTCCTT TGTCTTGGTA           120

GATCCCCTGC CATCTGGTTA TCAATTTAAT CCTGAAGCTA CAAAAGCTGC CAGCCCTGGC           180

TTTGATGTCG CTTATGATAA TGCAACTAAT ACAGTCACCT TCAAGGCAAC TGCAGCAACT           240

TTGGCTACGT TTAATGCTGA TTTGACTAAG TCAGTGGCAA CGATTTATCC AACAGTGGTC           300

GGACAAGTTC TTAATGATGG CGCAACTTAT                                            330

(2) INFORMATION FOR SEQ ID NO:16:

(i) SEQUENCE CHARACTERISTICS:
            (A) LENGTH: 240 base pairs
            (B) TYPE: nucleic acid
            (C) STRANDEDNESS: double
            (D) TOPOLOGY: linear (ii) MOLECULE TYPE: Genomic DNA (xi) SEQUENCE DESCRIPTION: SEQ ID NO:16:

ACAGAAAAGC CGTTGGAGCC AGCACCTGTT GAGCCAAGCT ATGAAGCAGA GCCAACGCCA            60

CCGACACCAA CACCAGATCA ACCAGAACCA AACAAACCTG TTGAGCCAAC TTATGAGGTT           120

ATTCCAACAC CGCCGACTGA TCCTGTTTAT CAAGATCTTC CAACACCTCC ATCTATACCA           180

ACTGTTCATT TCCATTACTT TAAACTAGCT GTTCAGCCGC AGGTTAACAA AGAAATTAGA           240

(2) INFORMATION FOR SEQ ID NO:17:

(i) SEQUENCE CHARACTERISTICS:
            (A) LENGTH: 390 base pairs
            (B) TYPE: nucleic acid
            (C) STRANDEDNESS: double
            (D) TOPOLOGY: linear (ii) MOLECULE TYPE: Genomic DNA (xi) SEQUENCE DESCRIPTION: SEQ ID NO:17:

ACAGAAAAGC CGTTGGAGCC AGCACCTGTT GAGCCAAGCT ATGAAGCAGA GCCAACGCCA            60

CCGACACCAA CACCAGATCA ACCAGAACCA AACAAACCTG TTGAGCCAAC TTATGAGGTT           120

ATTCCAACAC CGCCGACTGA TCCTGTTTAT CAAGATCTTC CAACACCTCC ATCTATACCA           180

ACTGTTCATT TCCATTACTT TAAACTAGCT GTTCAGCCGC AGGTTAACAA AGAAATTAGA           240

AACAATAACG ATGTTAATAT TGACAGAACT TTGGTGGCTA AACAATCTGT TGTTAAGTTC           300

CAGCTGAAGA CAGCAGATCT CCCTGCTGGA CGTGATGAAA CAACTTCCTT TGTCTTGGTA           360

GATCCCCTGC CATCTGGTTA TCAATTTAAT                                            390

(2) INFORMATION FOR SEQ ID NO:18:

(i) SEQUENCE CHARACTERISTICS:
        (A) LENGTH: 156 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:18:

```
GAAACCGGCA AAAAACCAAA TATTTGGTAT TCATTAAATG GTAAAATCCG TGCGGTTAAT      60
CTTCCTAAAG TTACTAAGGA AAAACCCACA CCTCCGGTTA AACCAACAGC TCCAACTAAA     120
CCAACTTATG AAACAGAAAA GCCATTAAAA CCGGCA                              156
```

(2) INFORMATION FOR SEQ ID NO:19:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:19:

```
CAAGATCTTC CAACACCTCC ATCTATACCA ACTGTTCATT TCCATTACTT TAAACTAGCT      60
GTTCAGCCGC AGGTTAACAA AGAAATTAGA AACAATAACG ATGTTAATAT TGACAGAACT     120
TTGGTGGCTA AACAATCTGT TGTTAAGTTC CAGCTGAAGA CAGCAGATCT CCCTGCTGGA     180
CGTGATGAAA CAACTTCCTT TGTCTTGGTA                                     210
```

(2) INFORMATION FOR SEQ ID NO:20:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:20:

```
TTCCAGCTGA AGACAGCAGA TCTCCCTGCT GGACGTGATG AAACAACTTC CTTTGTCTTG      60
GTA                                                                   63
```

(2) INFORMATION FOR SEQ ID NO:21:

(i) SEQUENCE CHARACTERISTICS:
        (A) LENGTH: 936 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:21:

```
GAAACCGGCA AAAAACCAAA TATTTGGTAT TCATTAAATG GTAAAATCCG TGCGGTTAAT      60
CTTCCTAAAG TTACTAAGGA AAAACCCACA CCTCCGGTTA AACCAACAGC TCCAACTAAA     120
CCAACTTATG AAACAGAAAA GCCATTAAAA CCGGCACCAG TAGCTCCAAA TTATGAAAAG     180
GAGCCAACAC CACCGACAAG AACACCGGAT CAAGCAGAGC CAAAGAAACC CACTCCGCCG     240
```

-continued

```
ACCTATGAAA CAGAAAAGCC GTTGGAGCCA GCACCTGTTG AGCCAAGCTA TGAAGCAGAG      300

CCAACACCGC CGACAAGGAC ACCGGATCAG GCAGAGCCAA ATAAACCCAC ACCGCCGACC      360

TATGAAACAG AAAAGCCGTT GGAGCCAGCA CCTGTTGAGC CAAGCTATGA AGCAGAGCCA      420

ACGCCACCGA CACCAACACC AGATCAACCA GAACCAAACA AACCTGTTGA GCCAACTTAT      480

GAGGTTATTC AACACCGCC GACTGATCCT GTTTATCAAG ATCTTCCAAC ACCTCCATCT       540

ATACCAACTG TTCATTTCCA TTACTTTAAA CTAGCTGTTC AGCCGCAGGT TAACAAAGAA      600

ATTAGAAACA ATAACGATGT TAATATTGAC AGAACTTTGG TGGCTAAACA ATCTGTTGTT      660

AAGTTCCAGC TGAAGACAGC AGATCTCCCT GCTGGACGTG ATGAAACAAC TTCCTTTGTC      720

TTGGTAGATC CCCTGCCATC TGGTTATCAA TTTAATCCTG AAGCTACAAA AGCTGCCAGC      780

CCTGGCTTTG ATGTCGCTTA TGATAATGCA ACTAATACAG TCACCTTCAA GGCAACTGCA      840

GCAACTTTGG CTACGTTTAA TGCTGATTTG ACTAAGTCAG TGGCAACGAT TTATCCAACA      900

GTGGTCGGAC AAGTTCTTAA TGATGGCGCA ACTTAT                                 936
```

(2) INFORMATION FOR SEQ ID NO:22:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:22:

```
CAAGATCTTC CAACACCTCC ATCTATACCA ACTGTTCATT TCCATTACTT TAAACTAGCT       60

GTTCAGCCGC AGGTTAACAA AGAAATTAGA                                         90
```

(2) INFORMATION FOR SEQ ID NO:23:

(i) SEQUENCE CHARACTERISTICS:
        (A) LENGTH: 1561 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Met Lys Val Lys Lys Thr Tyr Gly Phe Arg Lys Ser Lys Ile Ser Lys
 1               5                  10                  15

Thr Leu Cys Gly Ala Val Leu Gly Thr Val Ala Ala Val Ser Val Ala
            20                  25                  30

Gly Gln Lys Val Phe Ala Asp Glu Thr Thr Thr Ser Asp Val Asp
        35                  40                  45

Thr Lys Val Val Gly Thr Gln Thr Gly Asn Pro Ala Thr Asn Leu Pro
     50                  55                  60

Glu Ala Gln Gly Ser Ala Ser Lys Gln Ala Glu Gln Ser Gln Thr Lys
65                  70                  75                  80

Leu Glu Arg Gln Met Val His Thr Ile Glu Val Pro Lys Thr Asp Leu
                85                  90                  95

Asp Gln Ala Ala Lys Asp Ala Lys Ser Ala Gly Val Asn Val Val Gln
            100                 105                 110

Asp Ala Asp Val Asn Lys Gly Thr Val Lys Thr Ala Glu Glu Ala Val
        115                 120                 125

Gln Lys Glu Thr Glu Ile Lys Glu Asp Tyr Thr Lys Gln Ala Glu Asp
```

-continued

```
            130                 135                 140
Ile Lys Lys Thr Thr Asp Gln Tyr Lys Ser Asp Val Ala Ala His Glu
145                 150                 155                 160

Ala Glu Val Ala Lys Ile Lys Ala Lys Asn Gln Ala Thr Lys Glu Gln
                165                 170                 175

Tyr Gly Lys Asp Met Val Ala His Lys Ala Glu Val Glu Arg Ile Asn
            180                 185                 190

Ala Ala Asn Ala Ala Ser Lys Thr Ala Tyr Glu Ala Lys Leu Ala Gln
                195                 200                 205

Tyr Gln Ala Asp Leu Ala Ala Val Gln Lys Thr Asn Ala Ala Asn Gln
            210                 215                 220

Ala Ser Tyr Gln Lys Ala Leu Ala Ala Tyr Gln Ala Glu Leu Lys Arg
225                 230                 235                 240

Val Gln Glu Ala Asn Ala Ala Lys Ala Ala Tyr Asp Thr Ala Val
                245                 250                 255

Ala Ala Asn Asn Ala Lys Asn Thr Glu Ile Ala Ala Ala Asn Glu Glu
            260                 265                 270

Ile Arg Lys Arg Asn Ala Thr Ala Lys Ala Glu Tyr Glu Thr Lys Leu
                275                 280                 285

Ala Gln Tyr Gln Ala Glu Leu Lys Arg Val Gln Glu Ala Asn Ala Ala
290                 295                 300

Asn Glu Ala Asp Tyr Gln Ala Lys Leu Thr Ala Tyr Gln Thr Glu Leu
305                 310                 315                 320

Ala Arg Val Gln Lys Ala Asn Ala Asp Ala Lys Ala Ala Tyr Glu Ala
                325                 330                 335

Ala Val Ala Ala Asn Asn Ala Lys Asn Ala Ala Leu Thr Ala Glu Asn
            340                 345                 350

Thr Ala Ile Lys Gln Arg Asn Glu Asn Ala Lys Ala Thr Tyr Glu Ala
                355                 360                 365

Ala Leu Lys Gln Tyr Glu Ala Asp Leu Ala Ala Val Lys Lys Ala Asn
            370                 375                 380

Ala Ala Asn Glu Ala Asp Tyr Gln Ala Lys Leu Thr Ala Tyr Gln Thr
385                 390                 395                 400

Glu Leu Ala Arg Val Gln Lys Ala Asn Ala Asp Ala Lys Ala Ala Tyr
                405                 410                 415

Glu Ala Ala Val Ala Ala Asn Asn Ala Ala Asn Ala Ala Leu Thr Ala
                420                 425                 430

Glu Asn Thr Ala Ile Lys Lys Arg Asn Ala Asp Ala Lys Ala Asp Tyr
                435                 440                 445

Glu Ala Lys Leu Ala Lys Tyr Gln Ala Asp Leu Ala Lys Tyr Gln Lys
            450                 455                 460

Asp Leu Ala Asp Tyr Pro Val Lys Leu Lys Ala Tyr Glu Asp Glu Gln
465                 470                 475                 480

Ala Ser Ile Lys Ala Ala Leu Ala Glu Leu Glu Lys His Lys Asn Glu
                485                 490                 495

Asp Gly Asn Leu Thr Glu Pro Ser Ala Gln Asn Leu Val Tyr Asp Leu
            500                 505                 510

Glu Pro Asn Ala Asn Leu Ser Leu Thr Thr Asp Gly Lys Phe Leu Lys
            515                 520                 525

Ala Ser Ala Val Asp Asp Ala Phe Ser Lys Ser Thr Ser Lys Ala Lys
            530                 535                 540

Tyr Asp Gln Lys Ile Leu Gln Leu Asp Asp Leu Asp Ile Thr Asn Leu
545                 550                 555                 560
```

-continued

```
Glu Gln Ser Asn Asp Val Ala Ser Ser Met Glu Leu Tyr Gly Asn Phe
                565                 570                 575
Gly Asp Lys Ala Gly Trp Ser Thr Thr Val Ser Asn Asn Ser Gln Val
            580                 585                 590
Lys Trp Gly Ser Val Leu Leu Glu Arg Gly Gln Ser Ala Thr Ala Thr
        595                 600                 605
Tyr Thr Asn Leu Gln Asn Ser Tyr Tyr Asn Gly Lys Lys Ile Ser Lys
    610                 615                 620
Ile Val Tyr Lys Tyr Thr Val Asp Pro Lys Ser Lys Phe Gln Gly Gln
625                 630                 635                 640
Lys Val Trp Leu Gly Ile Phe Thr Asp Pro Thr Leu Gly Val Phe Ala
                645                 650                 655
Ser Ala Tyr Thr Gly Gln Val Glu Lys Asn Thr Ser Ile Phe Ile Lys
            660                 665                 670
Asn Glu Phe Thr Phe Tyr Asp Glu Asp Gly Lys Pro Ile Asn Phe Asp
        675                 680                 685
Asn Ala Leu Leu Ser Val Ala Ser Leu Asn Arg Glu Asn Asn Ser Ile
    690                 695                 700
Glu Met Ala Lys Asp Tyr Thr Gly Lys Phe Val Lys Ile Ser Gly Ser
705                 710                 715                 720
Ser Ile Gly Glu Lys Asn Gly Met Ile Tyr Ala Thr Asp Thr Leu Asn
                725                 730                 735
Phe Arg Gln Gly Gln Gly Gly Ala Arg Trp Thr Met Tyr Thr Arg Ala
            740                 745                 750
Ser Glu Pro Gly Ser Gly Trp Asp Ser Ser Asp Ala Pro Asn Ser Trp
        755                 760                 765
Tyr Gly Ala Gly Ala Ile Arg Met Ser Gly Pro Asn Asn Ser Val Thr
    770                 775                 780
Leu Gly Ala Ile Ser Ser Thr Leu Val Val Pro Ala Asp Pro Thr Met
785                 790                 795                 800
Ala Ile Glu Thr Gly Lys Lys Pro Asn Ile Trp Tyr Ser Leu Asn Gly
                805                 810                 815
Lys Ile Arg Ala Val Asn Leu Pro Lys Val Thr Lys Glu Lys Pro Thr
            820                 825                 830
Pro Pro Val Lys Pro Thr Ala Pro Thr Lys Pro Thr Tyr Glu Thr Glu
        835                 840                 845
Lys Pro Leu Lys Pro Ala Pro Val Ala Pro Asn Tyr Glu Lys Glu Pro
    850                 855                 860
Thr Pro Pro Thr Arg Thr Pro Asp Gln Ala Glu Pro Lys Lys Pro Thr
865                 870                 875                 880
Pro Pro Thr Tyr Glu Thr Glu Lys Pro Leu Glu Pro Ala Pro Val Glu
                885                 890                 895
Pro Ser Tyr Glu Ala Glu Pro Thr Pro Thr Arg Thr Pro Asp Gln
            900                 905                 910
Ala Glu Pro Asn Lys Pro Thr Pro Thr Tyr Thr Glu Lys Pro
        915                 920                 925
Leu Glu Pro Ala Pro Val Glu Pro Ser Tyr Glu Ala Glu Pro Thr Pro
    930                 935                 940
Pro Thr Pro Thr Pro Asp Gln Pro Glu Pro Asn Lys Pro Val Glu Pro
945                 950                 955                 960
Thr Tyr Glu Val Ile Pro Thr Pro Pro Thr Asp Pro Val Tyr Gln Asp
                965                 970                 975
```

-continued

```
Leu Pro Thr Pro Pro Ser Ile Pro Thr Val His Phe His Tyr Phe Lys
            980                 985                 990

Leu Ala Val Gln Pro Gln Val Asn Lys Glu Ile Arg Asn Asn Asn Asp
            995                1000                1005

Val Asn Ile Asp Arg Thr Leu Val Ala Lys Gln Ser Val Val Lys Phe
           1010                1015                1020

Gln Leu Lys Thr Ala Asp Leu Pro Ala Gly Arg Asp Glu Thr Thr Ser
1025                1030                1035                104

Phe Val Leu Val Asp Pro Leu Pro Ser Gly Tyr Gln Phe Asn Pro Glu
           1045                1050                1055

Ala Thr Lys Ala Ala Ser Pro Gly Phe Asp Val Ala Tyr Asp Asn Ala
           1060                1065                1070

Thr Asn Thr Val Thr Phe Lys Ala Thr Ala Thr Leu Ala Thr Phe
           1075                1080                1085

Asn Ala Asp Leu Thr Lys Ser Val Ala Thr Ile Tyr Pro Thr Val Val
           1090                1095                1100

Gly Gln Val Leu Asn Asp Gly Ala Thr Tyr Lys Asn Asn Phe Ser Leu
1105                1110                1115                112

Thr Val Asn Asp Ala Tyr Gly Ile Lys Ser Asn Val Val Arg Val Thr
           1125                1130                1135

Thr Pro Gly Lys Pro Asn Asp Pro Asp Asn Pro Asn Asn Tyr Ile
           1140                1145                1150

Lys Pro Thr Lys Val Asn Lys Asn Glu Asn Gly Val Ile Asp Gly
           1155                1160                1165

Lys Thr Val Leu Ala Gly Ser Thr Asn Tyr Tyr Glu Leu Thr Trp Asp
           1170                1175                1180

Leu Asp Gln Tyr Lys Asn Asp Arg Ser Ser Ala Asp Thr Ile Gln Gln
1185                1190                1195                120

Gly Phe Tyr Tyr Val Asp Asp Tyr Pro Glu Glu Ala Leu Glu Leu Arg
           1205                1210                1215

Gln Asp Leu Val Lys Ile Thr Asp Ala Asn Gly Asn Glu Val Thr Gly
           1220                1225                1230

Val Ser Val Asp Asn Tyr Thr Ser Leu Glu Ala Ala Pro Gln Glu Ile
           1235                1240                1245

Arg Asp Val Leu Ser Lys Ala Gly Ile Arg Pro Lys Gly Ala Phe Gln
           1250                1255                1260

Ile Phe Arg Ala Asp Asn Pro Arg Glu Phe Tyr Asp Thr Tyr Val Lys
1265                1270                1275                128

Thr Gly Ile Asp Leu Lys Ile Val Ser Pro Met Val Val Lys Lys Gln
           1285                1290                1295

Met Gly Gln Thr Gly Gly Ser Tyr Glu Asp Gln Ala Tyr Gln Ile Asp
           1300                1305                1310

Phe Gly Asn Gly Tyr Ala Ser Asn Ile Val Ile Asn Asn Val Pro Lys
           1315                1320                1325

Ile Asn Pro Lys Lys Asp Val Thr Leu Thr Leu Asp Pro Ala Asp Thr
           1330                1335                1340

Asn Asn Val Asp Gly Gln Thr Ile Pro Leu Asn Thr Val Phe Asn Tyr
1345                1350                1355                136

Arg Leu Ile Gly Gly Ile Ile Pro Ala Asn His Ser Glu Glu Leu Phe
           1365                1370                1375

Glu Tyr Asn Phe Tyr Asp Asp Tyr Asp Gln Thr Gly Asp His Tyr Thr
           1380                1385                1390

Gly Gln Tyr Lys Val Phe Ala Lys Val Asp Ile Thr Leu Lys Asn Gly
```

```
                   1395                1400                1405
        Val Ile Ile Lys Ser Gly Thr Glu Leu Thr Gln Tyr Thr Thr Ala Glu
                1410                1415                1420

Val Asp Thr Thr Lys Gly Ala Ile Thr Ile Lys Phe Lys Glu Ala Phe
        1425                1430                1435                144

Leu Arg Ser Val Ser Ile Asp Ser Ala Phe Gln Ala Glu Ser Tyr Ile
                    1445                1450                1455

Gln Met Lys Arg Ile Ala Val Gly Thr Phe Glu Asn Thr Tyr Ile Asn
                    1460                1465                1470

Thr Val Asn Gly Val Thr Tyr Ser Ser Asn Thr Val Lys Thr Thr Thr
                    1475                1480                1485

Pro Glu Asp Pro Ala Asp Pro Thr Asp Pro Gln Asp Pro Ser Ser Pro
                1490                1495                1500

Arg Thr Ser Thr Val Ile Ile Tyr Lys Pro Gln Ser Thr Ala Tyr Gln
        1505                1510                1515                152

Pro Ser Ser Val Gln Lys Thr Leu Pro Asn Thr Gly Val Thr Asn Asn
                    1525                1530                1535

Ala Tyr Met Pro Leu Leu Gly Ile Ile Gly Leu Val Thr Ser Phe Ser
                    1540                1545                1550

Leu Leu Gly Leu Lys Ala Lys Lys Asp
                    1555                1560

(2) INFORMATION FOR SEQ ID NO:24:

(i) SEQUENCE CHARACTERISTICS:
          (A) LENGTH: 4865 base pairs
          (B) TYPE: nucleic acid
          (C) STRANDEDNESS: double
          (D) TOPOLOGY: linear (ii) MOLECULE TYPE: Genomic DNA (xi) SEQUENCE DESCRIPTION: SEQ ID NO:24:

ATTTCAGCAA AAATTGACAA ATCAAATCAA TTATATTACA ATTTTTTAAC GTATATTACA      60

AAAATATATT TGGAAGATTT ATTCAGATTT GGAGGATTTA TGAAAGTCAA AAAAACTTAC    120

GGTTTTCGTA AAAGTAAAAT TAGTAAAACA CTGTGTGGTG CTGTTCTAGG AACAGTAGCA    180

GCAGTCTCTG TAGCAGGACA AAAGGTTTTT GCCGATGAAA CGACCACTAC TAGTGATGTA    240

GATACTAAAG TAGTTGGAAC ACAAACTGGA AATCCAGCGA CCAATTTGCC AGAGGCTCAA    300

GGAAGTGCGA GTAAGCAAGC TGAACAAAGT CAAACCAAGC TGGAGAGACA AATGGTTCAT    360

ACCATTGAAG TACCTAAAAC TGATCTTGAT CAAGCAGCAA AAGATGCTAA GTCTGCTGGT    420

GTCAATGTTG TCCAAGATGC CGATGTTAAT AAAGGAACTG TTAAAACAGC TGAAGAAGCA    480

GTCCAAAAAG AAACTGAAAT TAAAGAAGAT TACACAAAAC AAGCTGAGGA TATTAAGAAG    540

ACAACAGATC AATATAAATC GGATGTAGCT GCTCATGAGG CAGAAGTTGC TAAAATCAAA    600

GCTAAAAATC AGGCAACTAA AGAACAGTAT GGAAAAGATA TGGTAGCTCA TAAAGCCGAG    660

GTTGAACGCA TTAATGCTGC AAATGCTGCC AGTAAAACAG CTTATGAAGC TAAATTGGCT    720

CAATATCAAG CAGATTTAGC AGCCGTTCAA AAAACCAATG CTGCCAATCA AGCATCCTAT    780

CAAAAAGCCC TTGCTGCTTA TCAGGCTGAA CTGAAACGTG TTCAGGAAGC TAATGCAGCC    840

GCCAAAGCCG CTTATGATAC TGCTGTAGCA GCAAATAATG CCAAAAATAC AGAAATTGCC    900

GCTGCCAATG AAGAAATTAG AAAACGCAAT GCAACGGCCA AAGCTGAATA TGAGACTAAG    960

TTAGCTCAAT ATCAAGCTGA ACTAAAGCGT GTTCAGGAAG CTAATGCCGC AAACGAAGCA   1020
```

-continued

```
GACTATCAAG CTAAATTGAC CGCCTATCAA ACAGAGCTTG CTCGCGTTCA GAAAGCCAAT    1080

GCAGATGCTA AAGCGGCCTA TGAAGCAGCT GTAGCAGCAA ATAATGCCAA AAATGCGGCA    1140

CTTACAGCTG AAAATACTGC AATTAAGCAA CGCAATGAGA ATGCTAAGGC GACTTATGAA    1200

GCTGCACTCA AGCAATATGA GGCTGATTTG GCAGCGGTGA AAAAGCTAA TGCCGCAAAC    1260

GAAGCAGACT ATCAAGCTAA ATTGACCGCC TATCAAACAG AGCTCGCTCG CGTTCAAAAG    1320

GCCAATGCGG ATGCTAAAGC GGCCTATGAA GCAGCTGTAG CAGCAAATAA TGCCGCAAAT    1380

GCAGCGCTCA CAGCTGAAAA TACTGCAATT AAGAAGCGCA ATGCGGATGC TAAAGCTGAT    1440

TACGAAGCAA AACTTGCTAA GTATCAAGCA GATCTTGCCA AATATCAAAA AGATTTAGCA    1500

GACTATCCAG TTAAGTTAAA GGCATACGAA GATGAACAAG CTTCTATTAA AGCTGCACTG    1560

GCAGAACTTG AAAAACATAA AAATGAAGAC GGAAACTTAA CAGAACCATC TGCTCAAAAT    1620

TTGGTCTATG ATCTTGAGCC AAATGCGAAC TTATCTTTGA CAACAGATGG GAAGTTCCTT    1680

AAGGCTTCTG CTGTGGATGA TGCTTTTAGC AAAAGCACTT CAAAAGCAAA ATATGACCAA    1740

AAAATTCTTC AATTAGATGA TCTAGATATC ACTAACTTAG AACAATCTAA TGATGTTGCT    1800

TCTTCTATGG AGCTTTATGG CAATTTTGGT GATAAAGCTG GCTGGTCAAC GACAGTAAGC    1860

AATAACTCAC AGGTTAAATG GGGATCGGTA CTTTTAGAGC GCGGTCAAAG CGCAACAGCT    1920

ACATACACTA ACCTGCAGAA TTCTTATTAC GTCCAAGTTT CAAGGTCAAA AGGTTTGGTT    1980

AGGTATTTTT ACCGATCCAA AATGGTAAAA AGATTTCTAA AATTGTCTAC AAGTATACAG    2040

TGGACCCTAA CTTTAGGTGT TTTTGCTTCC GCTTATACAG GTCAAGTTGA AAAAAACACT    2100

TCTATTTTTA TTAAAAATGA ATTCACTTTC TATGACGAAG ATGGAAAACC AATTAATTTT    2160

GATAATGCCC TTCTATCAGT AGCTTCTCTT AACCGAGAAA ATAATTCTAT TGAGATGGCC    2220

AAAGATTATA CGGGTAAATT TGTCAAAATC TCTGGATCAT CTATCGGTGA AAAGAATGGC    2280

ATGATTTATG CTACAGATAC TCTCAACTTT AGGCAGGGTC AAGGTGGTGC TCGTTGGACC    2340

ATGTATACCA GAGCTAGCGA ACCGGGATCT GGCTGGGATA GTTCAGATGC GCCTAACTCT    2400

TGGTATGGTG CTGGTGCTAT CCGCATGTCT GGTCCTAATA ACAGTGTGAC TTTGGGTGCT    2460

ATCTCATCAA CACTTGTTGT GCCTGCTGAT CCTACAATGG CAATTGAAAC CGGCAAAAAA    2520

CCAAATATTT GGTATTCATT AAATGGTAAA ATCCGTGCGG TTAATCTTCC TAAAGTTACT    2580

AAGGAAAAAC CCACACCTCC GGTTAAACCA ACAGCTCCAA CTAAACCAAC TTATGAAACA    2640

GAAAAGCCAT TAAAACCGGC ACCAGTAGCT CCAAATTATG AAAAGGAGCC AACACCACCG    2700

ACAAGAACAC CGGATCAAGC AGAGCCAAAG AAACCCACTC CGCCGACCCTA TGAAACAGAA    2760

AAGCCGTTGG AGCCAGCACC TGTTGAGCCA AGCTATGAAG CAGAGCCAAC ACCGCCGACA    2820

AGGACACCGG ATCAGGCAGA GCCAAATAAA CCCACACCGC CGACCTATGA AACAGAAAAG    2880

CCGTTGGAGC CAGCACCTGT TGAGCCAAGC TATGAAGCAG AGCCAACGCC ACCGACACCA    2940

ACACCAGATC AACCAGAACC AAACAAACCT GTTGAGCCAA CTTATGAGGT TATTCCAACA    3000

CCGCCGACTG ATCCTGTTTA TCAAGATCTT CCAACACCTC CATCTATACC AACTGTTCAT    3060

TTCCATTACT TTAAACTAGC TGTTCAGCCG CAGGTTAACA AAGAAATTAG AAACAATAAC    3120

GATGTTAATA TTGACAGAAC TTTGGTGGCT AAACAATCTG TTGTTAAGTT CCAGCTGAAG    3180

ACAGCAGATC TCCCTGCTGG ACGTGATGAA ACAACTTCCT TTGTCTTGGT AGATCCCCTG    3240

CCATCTGGTT ATCAATTTAA TCCTGAAGCT ACAAAAGCTG CCAGCCCTGG CTTTGATGTC    3300

GCTTATGATA ATGCAACTAA TACAGTCACC TTCAAGGCAA CTGCAGCAAC TTTGGCTACG    3360

TTTAATGCTG ATTTGACTAA GTCAGTGGCA ACGATTTATC CAACAGTGGT CGGACAAGTT    3420
```

```
CTTAATGATG GCGCAACTTA TAAGAATAAT TTCTCGCTCA CAGTCAATGA TGCTTATGGC    3480

ATTAAATCCA ATGTTGTTCG GGTGACAACT CCTGGTAAAC CAAATGATCC AGATAACCCA    3540

AATAATAATT ACATTAAGCC AACTAAGGTT AATAAAAATG AAAATGGCGT TGTTATTGAT    3600

GGTAAAACAG TTCTTGCCGG TTCAACGAAT TATTATGAGC TAACTTGGGA TTTGGATCAA    3660

TATAAAAACG ACCGCTCTTC AGCAGATACC ATTCAACAAG GATTTTACTA TGTAGATGAT    3720

TATCCAGAAG AAGCGCTTGA ATTGCGTCAG GATTTAGTGA AGATTACAGA TGCTAATGGC    3780

AATGAAGTTA CTGGTGTTAG TGTGGATAAT TATACTAGTC TTGAAGCAGC CCCTCAAGAA    3840

ATTAGAGATG TTCTTTCTAA GGCAGGAATT AGACCTAAAG GTGCTTTCCA AATTTTCCGT    3900

GCCGATAATC CAAGAGAATT TTATGATACT TATGTCAAAA CTGGAATTGA TTTGAAGATT    3960

GTATCACCAA TGGTTGTTAA AAAACAAATG GGACAAACAG GCGGGAGTTA TGAAGATCAA    4020

GCTTACCAAA TTGACTTTGG TAATGGTTAT GCATCAAATA TCGTTATCAA TAATGTTCCT    4080

AAGATTAACC CTAAGAAAGA TGTGACCTTA ACACTTGATC CGGCTGATAC AAATAATGTT    4140

GATGGTCAGA CTATTCCACT TAATACAGTC TTTAATTACC GTTTGATTGG TGGCATTATC    4200

CCTGCAAATC ACTCAGAAGA ACTCTTTGAA TACAATTTCT ATGATGATTA TGATCAAACA    4260

GGAGATCACT ATACTGGTCA GTATAAAGTT TTTGCCAAGG TTGATATCAC TCTTAAAAAC    4320

GGTGTTATTA TCAAGTCAGG TACTGAGTTA ACTCAGTATA CGACAGCGGA AGTTGATACC    4380

ACTAAAGGTG CTATCACAAT TAAGTTCAAG GAAGCCTTTC TGCGTTCTGT TTCAATTGAT    4440

TCAGCCTTCC AAGCTGAAAG TTATATCCAA ATGAAACGTA TTGCGGTTGG TACTTTTGAA    4500

AATACCTATA TTAATACTGT CAATGGGGTA ACTTACAGTT CAAATACAGT GAAAACAACT    4560

ACTCCTGAGG ATCCTGCAGA CCCTACTGAT CCGCAAGATC CATCATCACC GCGGACTTCA    4620

ACTGTAATTA TCTACAAACC TCAATCAACT GCTTATCAAC CAAGCTCTGT CCAAAAAACG    4680

TTACCAAATA CGGGAGTAAC AAACAATGCT TATATGCCTT TACTTGGTAT TATTGGCTTA    4740

GTTACTAGTT TTAGTTTGCT TGGCTTAAAG GCTAAGAAAG ATTGACAGCA TAGATATTAC    4800

ATTAGAATTA AAAAGTGAGA TGAAGCGATA AATCACAGAT TGAGCTTTTA TCTCATTTTT    4860

TGATT                                                               4865
```

(2) INFORMATION FOR SEQ ID NO:25:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:25:

```
ATACATATGC CAACTGTTCA TTTCCATTAC TTT                                 33
```

(2) INFORMATION FOR SEQ ID NO:26:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:26:

```
                                             -continued
GCCATTGTCG ACTCATTCAT TTTTATTAAC CTTAGT                                36

(2) INFORMATION FOR SEQ ID NO:27:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:27:

His Gln Ala Ala Met Gln Ile Ile Arg Asp Ile Ile Asn Glu Glu Ala
 1               5                  10                  15

Ala Asp Trp Asp
            20
```

POLYPEPTIDE FRAGMENTS CAPABLE OF COMPETITION WITH *STREPTOCOCCUS MUTANS* ANTIGEN I/II

This invention relates to polypeptide fragments of the *Streptococcus mutans* I/II antigen that are useful in treating and preventing dental caries.

*Streptococcus mutans* is the main etiological agent of dental caries, a disease which affects mammals including humans.

The *S. mutans* I/II antigen (SA I/II) is a cell surface protein with an $M_r$ of about 185 kDa. It is believed to comprise several antigenic epitopes and to be at least partly responsible for *S. mutans* adhesion to teeth.

SA I/II is described in British Patent No. 2,060,647, as are number antibodies to it. A putative 3.5 to 4.5 kDa fragment of SA I/II, "antigen X", has also been described in European Patent No. 0 116 472.

However, it has now become clear that "antigen X" is not a fragment of SA I/II at all. Rather, it is a separate protein that merely co-purifies with SA I/II. It is believed to be encoded by a separate gene.

Two large fragments of SA I/II, an N-terminal fragment (residues 39 to 481) and a 40 kDa central fragment (residues 816 to 1213) are recognised by human serum antibodies. Within the central fragment, 80% of the sera tested recognise elements within a proline-rich region (residues 839–955) that comprises three tandem repeats. This suggests that this region includes one or more B-cell epitopes. The central fragment (residues 816–1213) is also believed to comprise one or more adhesion sites that mediate *S. mutans*' attachment to the tooth.

The aim of the above-mentioned work has been the development of vaccines for immunisation against dental caries. However, precise identification of the antigenic epitopes within SA I/II is a prerequisite for designing synthetic vaccines based on it. Similarly, precise identification of adhesion sites is essential for the design of drugs against dental caries that rely on inhibiting *S. mutans*' adhesion to the tooth.

No antigenic epitopes (T-cell or B-cell epitopes) or adhesion sites within SA I/II have been characterised, nor has the precise location of any such regions been suggested. Also, there has been no indication of the location of *S. mutans*' T-cell epitopes as the above-mentioned work has concentrated on *S. mutans*' ability to adhere to teeth and to generate a B-cell response.

The inventors have identified a number of T-cell epitopes, B-cell epitopes and adhesion sites within residues 803 to 1114 of SA I/II. Some of the T-cell and B-cell epitopes overlap or are contiguous with each other and/or with one or more of the adhesion sites.

The presence of a number of antigenic epitopes of both types and a number of adhesion sites within the same region of SA I/II could not have been predicted and the finding that some of the adhesion sites and epitopes overlap or are contiguous with each other is particularly surprising.

These findings make it possible to design effective synthetic vaccines against dental caries as well as drugs that engender resistance against the disease or alleviate pre-existing cases of it by preventing *S. mutans*' adhesion to the tooth. Further, the surprising finding that some of the T-antigenic epitopes and the adhesion site are contiguous or overlapping makes it possible to design bifunctional drugs that effect immunisation against dental caries as well as preventing adhesion of *S. mutans* to the tooth.

Accordingly, the present invention provides a nucleic acid sequence which codes upon expression in a prokaryoic or eukaryotic host cell for a polypeptide product having one or more properties selected from (i) the ability to adhere to a mammalian tooth in a competitive manner with naturally occurring *Streptococcus mutans* antigen I/II, thus preventing or diminishing the adhesion of *S.mutans* to the tooth; (ii) the ability to stimulate a T-cell response; and (iii) the ability to stimulate a B-cell response, said nucleic acid sequence being selected from:

(a) the sequences shown in SEQ. ID. Nos. 12 to 22 or the complementary strands thereof;

(b) nucleic acid sequences having a length of not more than 1000 base pairs which hybridise to the sequences defined in (a) over at least 70% of their length;

(c) nucleic acid sequences having a length of not more than 1000 base pairs which, but for the degeneracy of the genetic code, would hybridise to the nucleic acid sequences defined in (a) or (b) over at least 70% of their length and which sequences code for polypeptides having the same amino acid sequence code, would hybridise to the nucleic acid sequences defined in (a) or (b) over at least 70% of their length and which sequences code for polypeptides having the same amino acid sequence.

BRIEF DESCRIPTION OF THE DRAWINGS

FIG. 2A Mean S.I. (±sem) of PBMC from 30 subjects. Mean cpm with medium only was 538±112.

FIG. 2B Frequency of positive responses (S.I.≧3.0, cpm>500).

FIG. 6A SA I/II and recombinant fragment 984≠1161.

FIG. 6B Synthetic peptides.

Figure 1:
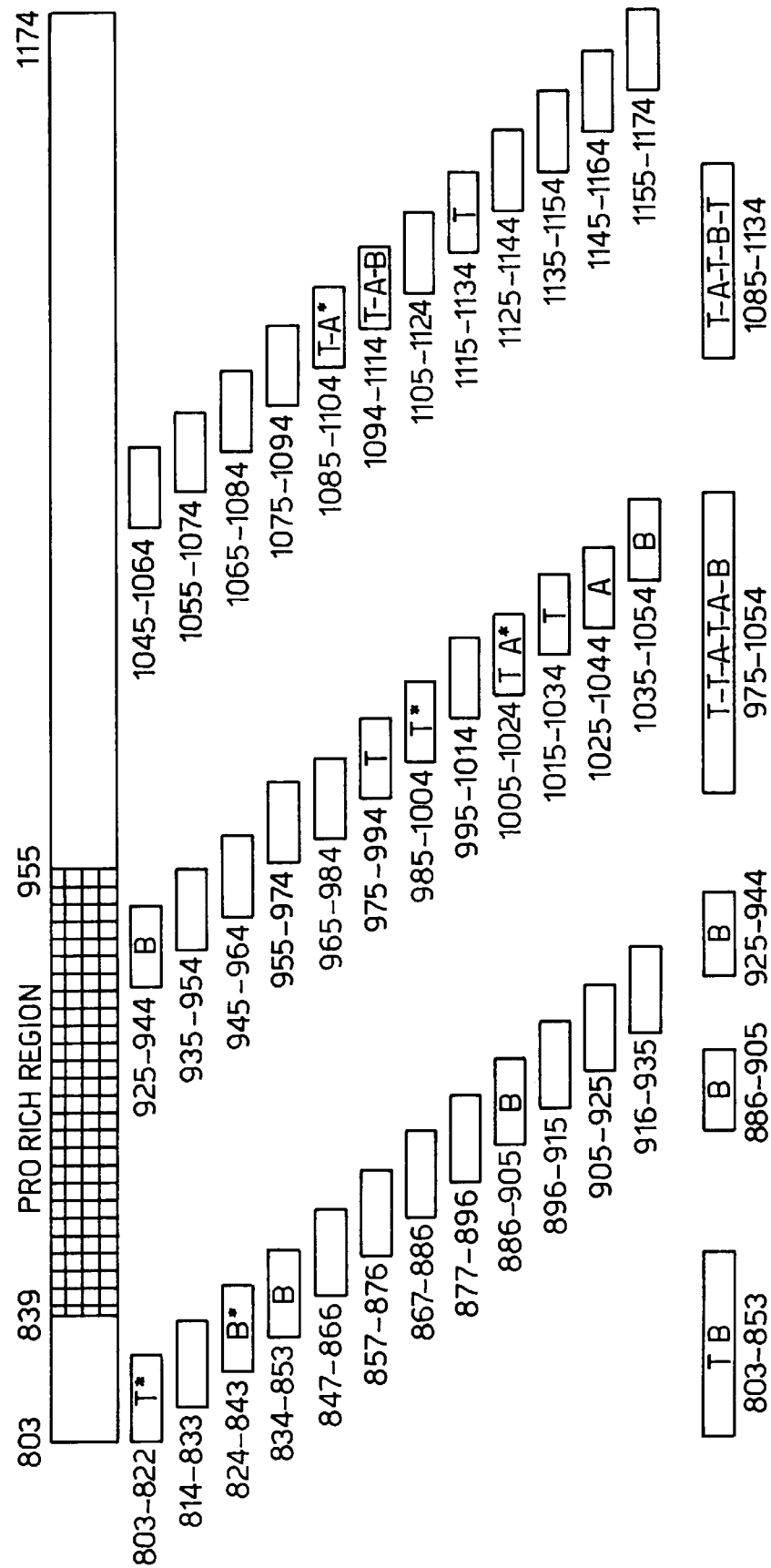
FIG. 1. Depiction of the panel of overlapping 20 mers used to map T-cell, B-cell and adhesion epitopes within SA I/II.

The polypeptides of the invention have one or more of the following properties. Firstly, they may have the ability to adhere to a mammalian tooth in a competitive manner with naturally occurring *Streptococcus mutans* antigen I/II, thus preventing or diminishing the adhesion of *S. mutans* to the tooth. Some of the peptides of the invention have been shown to inhibit adhesion of *S. mutans* to a tooth surface model (whole human saliva adsorbed to the wells of polystyrene microtitre plates or hydroxyapatite beads). Thus, these peptides comprise one or more adhesion sites and will adhere to a mammalian tooth in a competitive manner with naturally occurring SA I/II. Therefore, peptides according to the invention that comprise the adhesion site prevent or diminish the adhesion of *S. mutans* to the tooth. Peptides of the invention that comprise one or more adhesion epitopes include SEQ. ID. Nos. 1 to 6 and 8 to 10.

Secondly, peptides according to the invention may have the ability to stimulate a T-cell response. The inventors have shown that residues 803 to 854 and 925 to 1114 of SA I/II comprise a number of T-cell epitopes that are at least partially responsible for the T-cell response stimulated by the intact protein. Therefore, peptides according to the invention that comprise one or more of these the T-cell epitopes stimulate a T-cell response against *S. mutans* infection. Peptides of the invention that stimulate a T-cell response include those shown in SEQ ID Nos. 1 to 11.

Thirdly, the peptides of the invention may stimulate a B-cell response. The inventors have shown that residues 803 to 854 and 925 to 1114 of SA I/II comprise a number of B-cell epitopes and polypeptides according to the invention that comprise one or more B-cell epitopes stimulate a B-cell response against *S. mutans* infection. Peptides of the invention that comprise one or more B-cell epitopes include those shown in SEQ. ID. Nos. 1, 3 to 7 and 10.

The nucleic acid sequences of the present invention are preferably DNA, though they may be RNA. It will be obvious to those of skill in the art that, in RNA sequences according to the invention, the T residues shown in SEQ. ID. Nos. 12 to 22 will be replaced by U. Nucleic acid sequences of the invention will typically be in isolated or substantially isolated form. For example up to 80, up to 90, up to 95 or up to 100% of the nucleic acid material ir a preparation of a nucleic acid of the invention will typically be nucleic acid according to the invention.

Some preferred nucleic acid sequences of the invention are those shown in SEQ. ID. Nos. 12 to 22. However, the nucleic acid sequences of the present invention are not limited to these sequences. Rather, the sequences of the invention include sequences that are closely related to these sequences and that encode a polypeptide having at least one of the biological properties of naturally occurring SA I/II. These sequences may be prepared by altering those of SEQ ID Nos. 12 to 22 by any conventional method, or isolated from any organism or made synthetically. Such alterations, isolations or syntheses may be performed by any conventional method, for example by the methods of Sambrook et al (Molecular Cloning: A Laboratory Manual; 1989)

For example, the sequences of the invention include sequences that are capable of selective hybridisation to those of SEQ. ID. Nos. 12 to 22 or the complementary strands thereof and that encode a polypeptide having one or more of the properties defined above. Such sequences capable of selectively hybridizing to the DNA of SEQ. ID. Nos. 12 to 22 will generally be at least 70%, preferably at least 80 or 90% and more preferably at least 95% homologous to the DNA of SEQ. ID. Nos. 12 to 22 over a region of at least 10, preferably at least 20, 30, 40, 50 or more contiguous nucleotides.

Such sequences that hybridise to those shown in SEQ. ID. Nos. 12 to 22 will typically be of similar size to them, though they may be longer or shorter. However, if they are longer, they may not simply encode large fragments of native SA I/II amino acid sequence. Thus, sequences that hybridise to those of SEQ. ID. Nos. 12 to 22 may be sequences of up to 1000 bases in length, for example up to 950 or up to 933 bases in length, 933 bases being the length of the DNA sequence encoding the largest specifically identified peptide of the invention (SEQ. ID. No. 21). Also, sequences that hybridise to those of SEQ. ID. Nos. 12 to 22 must do so over at least 50% of their length, for example up to 60%, up to 70%, up to 80%, up to 90%, up to 95%, or up to 99% of their length.

Such hybridisation may be carried out under any suitable conditions known in the art (see Sambrook et al (1989): Molecular Cloning: A Laboratory Manual). For example, if high stringency is required, suitable conditions include 0.2×SSC at 60° C. If lower stringency is required, suitable conditions include 2×SSC at 60° C.

Also included within the scope of the invention are sequences that differ from those defined above because of the degeneracy of the genetic code and encode the same polypeptide having one or more of the properties defined above, namely the polypeptide of SEQ. ID. Nos. 1 to 11 or a polypeptide related to one of these polypeptides in any of the ways defined below.

Thus, the nucleic acid sequences of the invention include sequences which, but for the degeneracy of the genetic code, would hybridise to those shown in SEQ. ID. Nos. 12 to 22 or the complementary strands thereof. However, such sequences may not simply encode large fragments of native SA I/II amino acid sequences. Thus, these sequences may be up to 1000 bases in length, for example up to 950 or 933 bases in length. Also, their sequence must be such that, but of the degeneracy of the genetic code, they would hybridise to a sequence as shown in SEQ. ID. Nos. 12 to 22 over at least 50% of their length, for example, up to 60%, up to 70%, up to 80%, up to 90%, up to 95% or up to 99% of their length.

Also, the nucleic acid sequences of the invention include the complementary strands of the sequences defined above, for example the complementary strands of the nucleic acid sequences shown in SEQ. ID. Nos. 12 to 22.

Nucleic acid sequences of the invention will preferably be at least 30 bases in length, for example up to 50, up to 100, up to 200, up to 300, up to 400, up to 500, up to 600, up to 800 or up to 1000 bases.

Nucleic acid sequences of the invention may be extended at either or both of the 5' and 3' ends. Such extensions may be of any length. For example, an extension may comprise up to 10, up to 20, up to 50, up to 100, up to 200 or up to 500 or more nucleic acids. A 5' extension may have any sequence apart from that which is immediately 5' to the sequence of the invention (or the native sequence from which it is derived) in native SA I/II. A 3' extension may have any sequence apart from that which is 3' the sequence of SEQ. ID. No. 13 in native SA I/II. Thus, the nucleic acid sequences of the invention may be extended at either or both of the 5' and 3' ends by any non-wild-type sequence.

The polypeptides of the invention are encoded by the DNA sequences described above. Thus, the polypeptides of the invention are not limited to the polypeptides of SEQ. ID. Nos. 1 to 11 although these sequences represent preferred polypeptides. Rather, the polypeptides of the invention also include polypeptides with sequences closely related to those of SEQ. ID. Nos. 1 to 11 that have one or more of the biological properties of SA I/II. These sequences may be prepared by altering those of SEQ ID Nos. 1 to 11 by any conventional method, or isolated from any organism or made synthetically. Such alterations, isolations or syntheses may be performed by any conventional method, for example by the methods of Sambrook et al (Molecular Cloning: A Laboratory Manual; 1989). In particular, polypeptides related to those of SEQ ID Nos. 1 to 11 may be prepared by modifying DNA sequences as shown in SEQ ID Nos. 12 to 22 expressing them recombinantly.

The polypeptides of the invention may be encoded by nucleic acid sequences that have less than 100% sequence identity with those of SEQ. ID. Nos. 12 to 22. Thus, polypeptides of the invention may include substitutions, deletions, or insertions, that distinguish them from SEQ. ID. Nos. 1 to 11 as long as these do not destroy the biological property or properties that the polypeptides have in common with SA I/II.

A substitution, deletion or insertion may suitably involve one or more amino acids, typically from one to five, one to ten or one to twenty amino acids, for example, a substitution, deletion or insertion of one, two, three, four, five, eight, ten, fifteen, or twenty amino acids. Typically, a polypeptide of the invention has at least 60% at least 80%, at least 90%, or at least 95% sequence identity to the sequence of any one of SEQ. ID. Nos. 1 to 11.

In general, the physicochemical nature of the sequence of SEQ. ID. Nos. 1 to 11 should be preserved in a polypeptide of the invention. Such sequences will generally be similar in charge, hydrophobicity and size to that of SEQ. ID. Nos. 1 to 11. Examples of substitutions that do not greatly affect the physicochemical nature of amino acid sequences are those in which an amino acid from one of the following groups is substituted by a different amino acid from the same group:

H, R and K

I, L, V and M

A, G, S and T

D, E, Q and N.

However, it may be desirable to alter the physicochemical nature of the sequence of SEQ. ID. Nos. 1 to 11 in order to increase its therapeutic effectiveness. For example, many of the amino acids in the polypeptides of the invention are acidic. For example, residues 975 to 1044 (SEQ. ID. No. 8) as a whole are of an acidic nature. This acidity is believed to facilitate binding to a mammalian tooth. Thus, it may be desirable to increase the acidity of polypeptides of the invention by adding acidic residues or by substituting acidic residues for non-acidic ones. Acidic residues include aspartic acid and glutamic acid.

Where polypeptides of the invention are synthesised chemically, D-amino acids (which do not occur in nature) may be incorporated into the amino acid sequence at sites where they do not affect the polypeptides biological properties. This reduces the polypeptides' susceptibility to proteolysis by the recipient's proteases.

The nucleic acid sequences encoding the polypeptides of the invention may be extended at one or both ends by any non-wild-type sequence.

Thus, the polypeptides of the invention may be extended at either or both of the C- and N- termini by an amino acid sequence of any length. For example, an extension may comprise up to 5, up to 10, up to 20, up to 50, or up to 100 or 200 or more amino acids. An N-terminal extension may have any sequence apart from that which is N-terminal to the sequence of SEQ. ID. No. the invention (or the native sequence from which it is derived) in native SA I/II. A C-terminal extension may have any sequence apart from that which is C-terminal to the sequence of the invention (or the native sequence from which it is derived) in native SA I/II. Thus, the polypeptides of the invention may be extended at either or both of the C- and N- termini by any non-wild-type sequence.

The polypeptides of the invention may be attached to other polypeptides or proteins that enhance their antigenic properties. Thus, polypeptides of the invention may be attached to one or more other antigenic polypeptides. These additional antigenic polypeptides may be derived from *S. mutans* or from another organism. Possible additional antigenic polypeptides include heterologous T-cell epitopes derived from other *S. mutans* proteins or from species other than *S. mutans*. Heterologous B-cell epitopes may also be used. Such heterologous T-cell and or B-cell epitopes may be of any length and epitopes of up to 5, up to 10 or up to 20 amino acids in length are particularly preferred. These additional antiqenic polypeptides may be attached to the polypeptides of the invention chemically. Alternatively, one or more additional antigenic sequences may comprise an extension to a polypeptide of the invention.

A polypeptide of the invention may be subjected to one or more chemical modifications, such as glycosylation, sulphation, COOH-amidation or acylation. In particular, polypeptides that are acetylated at the N-terminus are preferred, as are polypeptides having C-terminal amide groups. Preferred polypeptides may have one or more of these modifications. For example, particularly preferred peptides may have a C-terminal amide group and N-terminal acetylation.

A polypeptide of the invention may form part of a larger polypeptide comprising multiple copies of the sequence of one or more of SEQ. ID. Nos. 1 to 11 or a sequences related to them in any of the ways defined herein.

Polypeptides of the invention typically comprise at least 15 amino acids, for example 15 to 20, 20 to 50, 50 to 100 or 100 to 200 or 200 to 300 amino acids. Preferred polypeptides include those shown in SEQ. ID. Nos. 1 to 11.

Polypeptides according to the invention may be purified or substantially purified. Such a polypeptide in substantially purified form will generally form part of a preparation in which more than 90%, for example up to 95%, up to 98% or up to 99% of the peptide material in the preparation is that of a polypeptide or polypeptides according to the invention.

The nucleic acid sequences and polypeptides of the invention were originally derived from *S. mutans*. However, nucleic acid sequences and/or polypeptides of the invention may also be obtained from other organisms, typically bacteria, especially other streptococci. They may be obtained either by conventional cloning techniques or by probing genomic or cDNA libraries with nucleic acid sequences according to the invention. This can be done by any conventional method, such as the methods of Sambrook et al (Molecular Cloning: A Laboratory Manual; 1989).

A nucleic acid sequence according to the invention may be included within a vector, suitably a replicable vector, for instance a replicable expression vector.

A replicable expression vector comprises an origin of replication so that the vector can be replicated in a host cell such as a bacterial host cell. A suitable vector will also typically comprise the following elements, usually in a 5' to 3' arrangement: a promoter for directing expression of the nucleic acid sequence and optionally a regulator of the promoter, a translational start codon and a nucleic acid sequence according to the invention encoding a polypeptide having one or more of the biological properties of SA I/II. A non-replicable vector lacks a suitable origin at replication whilst a non-expression vector lacks an effective promoter.

The vector may also contain one or more selectable marker genes, for example an ampicillin resistance gene for the identification of bacterial transformants. One particular preferred marker gene is the kanamycin resistance gene. Optionally, the vector may also comprise an enhancer for the promoter. If it is desired to express the nucleic acid sequence of the invention in a eucaryotic cell, the vector may also comprise a polyadenylation signal operably linked 3' to the nucleic acid encoding the functional protein. The vector may also comprise a transcriptional terminator 3' to the sequence encoding the polypeptide of the invention.

The vector may also comprise one or more non-coding sequences 3' to the sequence encoding the polypeptide of the invention. These may be from *S. mutans* (the organism from which the sequences of the invention are derived) or the host organism which is to be transformed with the vector or from another organism.

In an expression vector, the nucleic acid sequence of the invention is operably linked to a promoter capable of expressing the sequence. “Operably linked” refers to a juxtaposition wherein the promoter and the nucleic acid sequence encoding the polypeptide of the invention are in a relationship permitting the coding sequence to be expressed under the control of the promoter. Thus, there may be elements such as 5' non-coding sequence between the promoter and coding sequence. These elements may be native either to *S. mutans* or to the organism from which the promoter sequence is derived or to neither organism. Such sequences can be included in the vector if they enhance or do not impair the correct control of the coding sequence by the promoter.

The vector may be of any type. The vector may be in linear or circular form. For example, the vector may be a plasmid vector. Those of skill in the art will be able to prepare suitable vectors comprising nucleic acid sequences encoding polypeptides of the invention starting with widely available vectors which will be modified by genetic engineering techniques such as those described by Sambrook et al (Molecular Cloning: A Laboratory Manual; 1989). Preferred starting vectors include plasmids that confer kanamycin resistance and direct expression of the polypeptide of the invention via a tac promoter.

In an expression vector, any promoter capable of directing expression of a sequence of the invention in a host cell may be operably linked to the nucleic acid sequence of the invention. Suitable promoters include the tac promoter.

Such vectors may be used to transfect or transform a host cell. Depending on the type of vector, they may be used as cloning vectors to amplify DNA sequences according to the invention or to express this DNA in a host cell.

A further embodiment of the invention provides host cells harbouring vectors of the invention, i.e. cells transformed or transfected with vectors for the replication and/or expression of nucleic acid sequences according to the invention, including the sequences shown in SEQ. ID. Nos. 12 to 22. The cells will be chosen to be compatible with the vector and may for example be bacterial cells. Transformed or transfected bacterial cells, for example *E. coli* cells, will be particularly useful for amplifying nucleic acid sequences of the invention as well as for expressing them as polypeptides.

The cells may be transformed or transfected by any suitable method, such as the methods described by Sambrook et al (Molecular cloning: A Laboratory Manual; 1989). For example, vectors comprising nucleic acid sequences according to the invention may be packaged into infectious viral particles, such as retroviral particles. The constructs may also be introduced, for example, by electroporation, calcium phosphate precipitation, biolistic methods or by contacting naked nucleic acid vectors with the cells in solution.

In the said nucleic acid vectors with which the host cells are transformed or transfected, the nucleic may be DNA or RNA, preferably DNA.

The vectors with which the host cells are transformed or transfected may be of any suitable type. The vectors may be able to effect integration of nucleic acid sequences of the invention into the host cell genome or they may remain free in the cytoplasm. For example, the vector used for transformation may be an expression vector as defined herein.

The present invention also provides a process of producing polypeptides according to the invention. Such a process will typically comprise transforming or transfecting host cells with vectors comprising nucleic acid sequences according to the invention and expressing the nucleic acid sequence in these cells. In this case, the nucleic acid sequence will be operably linked to a promoter capable of directing its expression in the host cell. Desirably, such a promoter will be a “strong” promoter capable of achieving high levels of expression in the host cell. It may be desirable to overexpress the polypaptide according to the invention in the host cell. Suitable host cells for this purpose include yeast cells and bacterial cells, for example *E. coli* cells, a particularly preferred *E. coli* strain being *E. coli* K12 strain BL 21. However, other expression systems can also be used, for example baculovirus systems in which the vector is a baculovirus having in its genome nucleic acid encoding a polypeptide of the invention and expression occurs when the baculovirus is allowed to infect insect cells.

The thus produced polypeptide of the invention may he recovered by any suitable method known in the art. Optionally, the thus recovered polypeptide may be purified by any suitable method, for example a method according to Sambrook et al (Molecular Cloning: A Laboratory Manual).

The polypeptides of the invention may also be synthesised chemically using standard techniques of peptide synthesis. For shorter polypeptides, chemical synthesis may be preferable to recombinant expression. In particular, peptides of up to 20 or up to 40 amino acid residues in length may desirably be synthesised chemically.

The nucleic acid sequences of the invention may be used to prepare probes and primers. These will be useful, for example, in the isolation of genes having sequences similar to that of SEQ. ID. No. 24. Such probes and primers may be of any suitable length, desirably from 10 to 100, for example from 10 to 20, 20 to 50 or 50 to 100 bases in length.

The present invention also provides antibodies to the polypeptides of the invention. These antibodies may be monoclonal or polyclonal. For the purposes of this invention, the term “antibody”, includes fragments of whole antibodies which retain their binding activity for a target antigen. Such fragments include Fv, F(ab') and $F(ab')_2$ fragments, as well as single chain antibodies.

The antibodies may be produced by any method known in the art, such as the methods of Sambrook et al (Molecular Cloning: A Laboratory Manual; 1989). For example, they may be prepared by conventional hybridoma techniques or, in the case of modified antibodies or fragments, by recombinant DNA technology, for example by the expression in a suitable host vector of a DNA construct encoding the modified antibody or fragment operably linked to a promoter. Suitable host cells include bacterial (for example *E.* coli), yeast, insect and mammalian cells. Polyclonal antibodies may also be prepared by conventional means which comprise inoculating a host animal, for example a rat or a rabbit, with a peptide of the invention and recovering immune serum.

The present invention also provides pharmaceutical compositions comprising polypeptides of the invention. Three types of pharmaceutical compositions are particularly preferred. Firstly, compositions comprising polypeptides of the invention that include T-cell and/or B-cell epitopes may be used as vaccines against dental caries. Secondly, compositions comprising polypeptides of the invention that comprise adhesion sites will prevent or diminish adhesion of *S. mutans* to the tooth and can be used in the treatment of pre-existing cases of dental caries. Thirdly, compositions comprising polypeptides of the invention that include both one or more antigenic (T-cell or B-cell) epitopes and one or more adhesion epitopes can be used to effect vaccination against dental caries at the same time as caring pre-existing cases of the disease. A similar effect can be achieved by including in a composition one (or more peptides comprising one or more antigenic epitopes and one or more peptides comprising one or more adhesion sites.

A range of mammalian species can be vaccinated against dental caries using the polypeptides of the invention. Vaccination of humans is particularly desirable.

The compositions of the invention may be administered to mammals including humans by any route appropriate. Suitable routes include topical application in the mouth, oral delivery by means of tablets or capsule and parenteral delivery, including subcutaneous, intramuscular, intravenous and intradermal delivery. Preferred routes of administration are topical application in the mouth and injection, typically subcutaneous or intramuscular injection, with a view to effecting systemic immunisation.

As previously indicated, polypeptides according to the invention may also be mixed with other antigens of different immunogenicity.

The compositions of the invention may be administered to the subject alone or in a liposome or associated with other delivery molecules. The effective dosage depends on many factors, such as whether a delivery molecule is used, the route of delivery and the size of the mammal being vaccinated. Typical doses are from 0.1 to 100 mg of the polypeptide of the invention per dose, for example 0.1 to 1 mg, and 1 to 5 mg, 5 to 10 mg and 10 to 100 mg per dose. Doses of from 1 to 5 mg are preferred.

Dosage schedules will vary according to, for example, the route of administration, the species of the recipient and the condition of the recipient. However, single doses and multiple doses spread over periods of days, weeks or months are envisaged. A regime for administering a vaccine composition of the invention to young human patients will conveniently be :6 months, 2 years, 5 years and 10 years, with the initial dose being accompanied by adjuvant and the subsequent doses being about ½ to ¼ the level of polypeptide in the initial dose. The frequency of administration can, however, be determined by monitoring the antibody levels in the patient.

Where the peptides of the invention are to be applied topically in the mouth, one preferred dosage regime is to apply one or more polypeptides of the invention on two or more occasions, for example 2 to 10 occasions over a period of a few weeks, for example one to six weeks. A particularly preferred regime of this type involves six applications of a polypeptide of the invention over a period of three weeks.

Typical doses for each topical application are in the range of 0.1 to 100 mg for example 0.1 to 1 mg, 1 to 10 mg and 10 to 100 mg. Doses of from 1 to 5 mg for each application are preferred.

While it is possible for polypeptides of the invention to be administered alone it is preferable to present them as pharmaceutical formulations. The formulations of the present invention comprise at least one active ingredient, a polypeptide of the invention, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes.

Formulations suitable for parenteral administration include aqueous and non-aqueous sterile injection solutions which may contain anti-oxidants, buffers, bacteriostatis, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs.

In particular, the polypeptides of the invention may be coupled to lipids or carbohydrates. This increases their ability to adhere to teeth, either by prolonging the duration of the adhesion or increasing its affinity, or both. This is particularly desirable for shorter polypeptides of the invention, which comprise up to around 40 amino acid residues.

Of the possible formulations, sterile pyrogen-free aqueous and non-aqueous solutions are preferred. Also preferred are formulations in which the polypeptides of the invention are contained in liposomes. Injection solutions and suspensions may be prepared extemporaneously from sterile powders, granules and tablets of the kind previously described.

Oral methods of administration may produce an effect systemically or locally in the mouth. Orally active preparations can be formulated in any suitable carrier, such as a gel, toothpaste, mouthwash or chewing gum.

It should be understood that in addition to the ingredients particularly mentioned above the formulations of this invention may include other agents conventional in the art having regard to the type of formulation in question.

Accordingly, the present invention provides a method of vaccinating a mammalian host against dental caries or treating dental caries, which method comprises administering to the host an effective amount of a pharmaceutical composition as described above, for example a vaccine composition.

Antibodies, including monoclonal antibodies, can be formulated for passive immunisation as indicated above for the formulation of including polypeptides of the invention. Preferred formulations for passive immunisation include solid or liquid formulations such as gels, toothpastes, mouthwashes or chewing gum.

A further aspect of the present invention is a naked nucleic acid vaccine. In this embodiment, the vaccine composition comprises a nucleic acid, typically an isolated nucleic acid, preferably DNA, rather than a polypeptide. The nucleic acid is injected in to a mammalian host and expressed in vivo, generating a polypeptide of the invention. This stimulates a T-cell response, which leads to protective immunity against dental caries in the same way as direct vaccination with a polypeptide of the invention.

Naked nucleic acid vaccination can be carried out with any nucleic acid according to the invention as long as it encodes a polypeptide that stimulates a T-cell and or B-cell response. Preferred nucleic acids are those shown in SEQ. ID Nos. 1 to 11. These will typically be included within an expression vectors as defined above. In such an expression vector, the nucleic acid according to the invention will typically be operably linked to a promoter capable of directing its expression in a mammalian host cell. For example, promoters from viral genes that are expressed in the mammalian cells such as the cytomegalovirus (CMV) immediate early gene promoter are suitable. Also suitable are promoters from mammalian genes that are expressed in many or all mammalian cell types such as the promoters of "housekeeping" genes. One such promoter is the p-hydroxymethyl-CoA-reductase(HMG) promoter (Gautier et al (1989): Nucleic Acids Research; 17,8839).

For naked nucleic acid vaccination, it is preferred that the nucleic acid sequence according to the invention is incorporated into a plasmid vector, since it has been found that covalent closed circle (CCC) plasmid DNA can be taken up directly by muscle cells and expressed without being integrated into the cells' genomic DNA (Ascadi et al (1991): The New Biologist; 3, 71–81). Naked nucleic acid vaccine may be prepared as any of the types of formulation mentioned above in respect of conventional polypeptide-based vaccines. However, formulations suitable for parenteral injection, especially intramuscular injection, are preferred. Naked nucleic acid vaccines may be delivered in any of the ways mentioned above in respect of conventional polypeptide-based vaccines but intramuscular injection is preferred.

Accordingly, the present invention provides a vaccine composition comprising a nucleic acid sequence or vector as described above and an acceptable carrier.

The following examples illustrate the invention.

EXAMPLES

Materials and Methods

Materials

Fmoc amino acids, benzotrlazole-1-yl-oxy-trispyrrolidino-phosphonium hexaflurophosphate (PyBOP) and Rink Amide MBHA resin were purchased from Calbiochem-Novabiochem (UK) Ltd., (Nottingham, UK) Dimethylformamide, trifluoroacetic acid, diethyl ether, dichloromethane and piperidene were purchased from Romil Chemicals Ltd (Loughborough, UK). Di-isopropylethylamine was from Aldrich Chemical Co. (Dorset, UK). Oligonucleotides were purchased from Oswel DNA service (University of Edinburgh, Edinburgh, UK).

Bacteria and Growth Conditions

S.mutans Guy's strain (serotype c) were grown in 10 L basal medium as described previously (Russel et al (1978): Arch. Oral Biol., 2317; Russel et al (1980): Infect, Immun. 61, 5490) at 37° C. for 72 h for SA I/II preparation. For the adhesion assay, S. mutans were grown in Todd-Hewitt broth (Difco Laboratories, Detroit, Mich.). Escherichia coli BL21 (DE3) (Novagen Inc., Madison, Wis.) harbouring pET15b were grown at 37° C. in Luria-Bertani broth supplemented with carbenicillin (50 µg/ml) and recombinant protein expression was induced with isoppropyl-β-D-thiogalactopryanoside (1 mM).

Antigens

SA I/II was prepared from S. mutans (serotype c, Guy's strain) as described by Russel et al (1980: Infect. Immun. 28, 486). Using the procedure of Munro et al (1993: Infect. Immun. 61, 4590), the portion of the gene encoding residues 984–1161 was amplified by using the oligonucleotide primers: (5') ATACATATGCCAACGTTCATTTCCATTACTTT (SEQ. ID. No. 25) and (3') GCCATTGTCGACTCAT-TCATTTTTATTAACCTTAGT (SEQ. ID. No. 26), cloned into pET15b (modified by the addition of a Sal I site) and expressed in E. coli.

Synthetic Peptides

Peptide amides (20 mers overlapping by 10 residues) were synthesised on Rink amide MBHA resin in sealed porous polypropylene bags by the manual simultaneous multiple peptide synthesis procedure (Houghten (1985) PNAS 892, 5131) using Fmoc chemistry. PyBOP was used as coupling agent and Fmoc amino acids were activated In situ by addition of diisopropylethylamine. Following 20 cycles of synthesis, resin was washed with dimethylformamide followed by dichloromethane and peptides were cleaved by incubation in trifluoroacetic acid-ethanedithiol-anisolephenol-$H_2O$ (82.5:2.5:5:5:5; v/v/v/w/v) for 2 h at room temperature. Peptides were precipitated by the addition of 5 volumes ether, recovered by centrifugation and washed three times with ether. Finally, peptides were dissolved in water and lyophilised. The scale of synthesis was 50 µmol. Aliquots of each peptide were hydrolysed in 6M HCl at 110° C. for 24 h and compositions were determined using the Beckman 121MB automated analyser (Beckman Instruments Ltd, Bucks, UK). In each case the composition matched that predicted.

Antibodies

MAbs, L243 (anti-MHC class II) and W6/32 (anti-MHC class I) were produced from cultures of hybridomas obtained from the American Type Culture Collection (Rockville, Md, USA). ID4 an isotype (IgG2a) matched control of irrelevant specificity was provided by Dr. P. Shepherd (Department of Immunology, UMDS, Guys Hospital, London, UK). Rabbit anti-SA I/II antiserum was prepared as described previously (Russel et al (1980). Infect. Immun. 28, 486).

Lymphoproliferative Assay

Defibrinated blood from volunteers was separated on a Ficoll gradient. Sera was used for antibody assays (see below) while peripheral blood mononuclear cells (PBMCs) were washed and resuspended in RPMI 1640 (Sigma Chemical Co., St. Louis, Mo., USA) supplemented with 2 mM L-glutamine, penicillin (100 IU/ml), streptomycin sulphate (100 µg/ml) and 10% heat-inactivated autologous serum. PBMCs ($10^5$ cells/well) were cultured in 96-well round-bottomed plates (Costar, Cambridge, Mo., USA) in a total volume of 200 µl. Three replicates of each culture were incubated with three concentrations (1, 10 and 40 µg/ml) of SA I/II, recombinant fragments, non-recombinant control or synthetic peptides. Incubation was at 37° C. in a humidified atmosphere with 5% $CO_2$ for 6 days. Each culture received 0.2 µCi (7.4 kBq) of [$^3$H]-thymidine (Amersham International, Bucks, UK) 6 h before harvesting. Cultures were harvested onto glass fibre filters using a Dynatech (Chantilly, Va., USA) Minimal Cell harvester and [$^3$H]-thymidine incorporation was measured using the LKB liquid scintillation counter (Bromma, Sweden). Proliferation was expressed as stimulation index which is mean counts per minute (cpm) of antigen-stimulated, divided by, cpm of antigen-free cultures. Concanavalin A (10 µg/ml) (Sigma Chemical Co., St. Louis, Mo., USA) was used with every culture as a positive control but the results are not presented.

MHC dependency of proliferative responses to SA I/II was determined by culturing cells with antigen (10 µg/ml) as above in the presence of MAbs L235, W6/32 or ID4 at 1, 10 and 20 µg/ml. Cultures were incubated with [$^3$H]-thymidine, harvested and [$^3$H]-thymidine uptake was determined as described above.

ELISA for Serum Antibodies

Antibody recognition of synthetic peptides was determined by ELISA. Peptides (10 µg/ml) in phosphate buffered saline (PBS) were adsorbed to wells of polystyrene microtitre plates (Dynatech) for 2 h at room temperature. Plates were washed and wells were treated with 1.5% (w/v) bovine serum albumen (BSA) for 1 h at room temperature to block unbound sites. After washing, bound peptides were incubated with serially diluted sera in duplicate. Bound IgG antibodies were determined by incubation with alkaline phosphate conjugated-goat anti-human Ig (Sigma Chemical Co.) and subsequent reaction with paranitrophenyl phosphate (Sigma Chemical Co.). Plates were read at 405 nm using the microplate reader model 450 (Bio-Rad). After initial screening, the assay was repeated at least 3 times with each serum using a restricted set of peptides. SA I/II (2 $\mu$g/ml) was included in each assay as was an irrelevant peptide (HQAAMQIIRDIINEEAADWD (SEQ. ID. No. 27) derived from the sequence of SIV p27. Results are expressed as the highest dilution giving an absorbance $\geq 0.2$.

Western Blotting

Serum antibody responses were also assayed by Western blotting using SA I/II, the recombinant polypeptides and a control fraction from *E. coli* BL21 harbouring non-recombinant pET15b. Purified antigens were separated by sodium dodecyl sulphate-polyacrylamide gel electrophoresis (SDS-PAGE) with gels of 10% acrylamide, by using a mini-gel system (Hoeffer Scientific Instruments, San Francisco, Calif., USA). Proteins were transferred to nitrocellulose with a semi-dry blotter (Sartorius A. G., Gottingen, Germany). Nitrocellulose strips were blocked with 5% (wt/vol) nonfat milk powder 2.5% (wt/vol) BSA in Tris-HCl-buffered saline (pH 8.0) containing 0.05% (wt/vol) Tween 20. Strips were subsequently incubated with human sera (1 in 20 dilution) or rabbit anti-SA I/II antiserum ($10^{-4}$ dilution) and bound antibody was visualised by using alkaline phosphatase-conjugated secondary antibody with 5-bromo-4-chloro-3-indolylphosphate and nitroblue tetrazolium (Sigma Chemical Co.) as substrates. Each sera was assayed three times and responses were considered as positive if bands were visible in at least two assays.

Bacterial Adherence Assay

SA I/II mediated adherence of *S. mutans* (Guy's strain) to saliva was assayed by determining binding of [$^3$H]-thymidine labelled bacteria to saliva adsorbed to microtitre wells. Freshly collected human saliva from a single donor was clarified by centrifugation for 10 min at 3000 g, heat-inactivated at 60° C. for 30 min and finally clarified by centrifugation at 17,000 g for 20 min. Treated saliva was diluted with an equal volume of PBS and adsorbed to the wells of a polystyrene 96-well flat-bottomed microtitre plate (Immulon 4; Dynatech) for 2 h at room temperature. After coating, wells were washed three times with PBS and unbound sites were blocked by incubation with 1.5% (wt/vol) BSA in PBS for 1 h at room temperature. Plates were then washed three times with 50 mM KCl-1 mM CaCl$_2$-38 mM MgCl$_2$-1 mM KH$_2$PO$_4$-1.2 mM K$_2$PO$_4$ (pH 7.2; adherence buffer). *S. mutans* cells from an overnight culture in Todd-Hewitt broth were used to inoculate (1/10 volume) a further culture in Todd-Hewitt broth containing 100 $\mu$Ci (3.7 MBq) [$^3$H]-thymidine (Amersham International plc) per ml. Cells were harvested in late log phase (O.D. 700 nm approximately 0.4) pelleted by centrifugation at 100 g for 10 min and washed three times in adherence buffer. The final suspension was vortexed with 0.5 volume glass beads to break up chains of cocci which was monitored microscopically (Munro et al (1993): Infect. Immun. 61, 4590). Cells were resuspended to $5 \times 10^4$ c.p.m. per 50 $\mu$l and BSA was added to 1.5% (wt/vol). Specific activity of the washed *S. mutans* cells was estimated to be $1.3 \times 10^{-3}$ c.p.m. per cell (Munro et al (1985): Infect. Immun. 61, 4590). In competitive inhibition of adherence, the various synthetic peptides were added to the wells (at final concentrations 62.5–500 $\mu$M) in 50 $\mu$l adherence buffer containing 1.5% (wt/vol) BSA together with 50 $\mu$l radiolabelled *S. mutans* suspension. Microtitre plates were incubated at 37° C. for 2 h with gentle shaking and subsequently were washed ten times with adherence buffer. Bound *S. mutans* cells were eluted with 1% (wt/vol) SDS and transferred to glass fibre filters by using the Micromate 196 cell harvester (Canberra Packard, Berks, UK). Filters were counted using the Matrix 96 direct beta counter (Canberra Packard). Background binding was determined on wells to which no saliva was adsorbed. The percentage of binding of *S. mutans* to saliva was calculates by the formula [(test c.p.m.)—(control c.p.m.)/ total c.p.m.]×100. Percent inhibition of adherence was calculated as [(percent adherence without inhibitor-percent adherence with inhibitor)/percent adherence without inhibitor]×100. For proteins, determinations of streptococcal adhesion were made in triplicate or quadruplicate at each protein concentration while for peptides, duplicate determinations were made. In each case the assay was performed at least three times.

Statistics

The student's t test was used to analyse results.

Example 1

Preparation of a Panel of Overlapping Synthetic Peptides and Analysis of their Properties T Cell Epitope Mapping A panel of 32 overlapping synthetic peptides, spanning residues 803–1174 of SA I/II, was prepared, as described above (See FIG. 1). Proliferative responses of PBMCs from 30 subjects were determined by stimulation with peptides (see FIG. 2). All subjects responded to at least one peptide with a band range of 1–8 peptides, and a mean of 4.4 peptides. On the basis of frequency of response to each peptide (SI$\geq$3.0 c.p.m.>500) 3 immunodonminant epitopes were identified; peptides 803–822, 975–994 and 985–1004, each yielding frequencies>50% (FIG. 1). Since most (13/15) subjects who responded to peptide 975–994 also responded to peptide 985–1004, it is probable that a single T-cell epitope is present within residues 975–1004. Minor T cell epitopes were also identified within peptides 1005–1024, 1015–1034, 1085–1104 and 1115–1134 with frequencies>20% and some of the adjacent peptides may represent single T cell epitopes.

Figure 3:
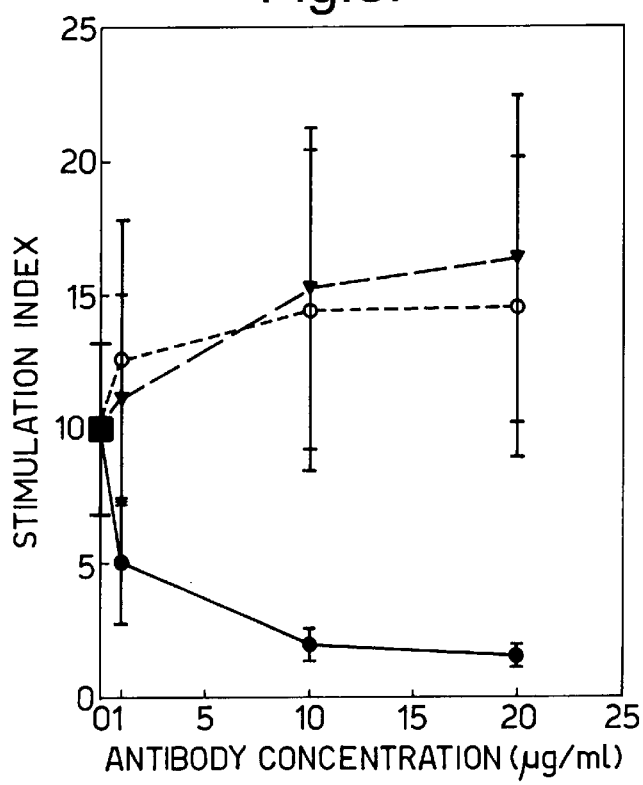
FIG. 3. MHC class II dependency of proliferative responses to SA I/II.

MHC Restriction of the Lymphoproliferative Responses (See FIG. 3 and Table 2)

Figure 2A:
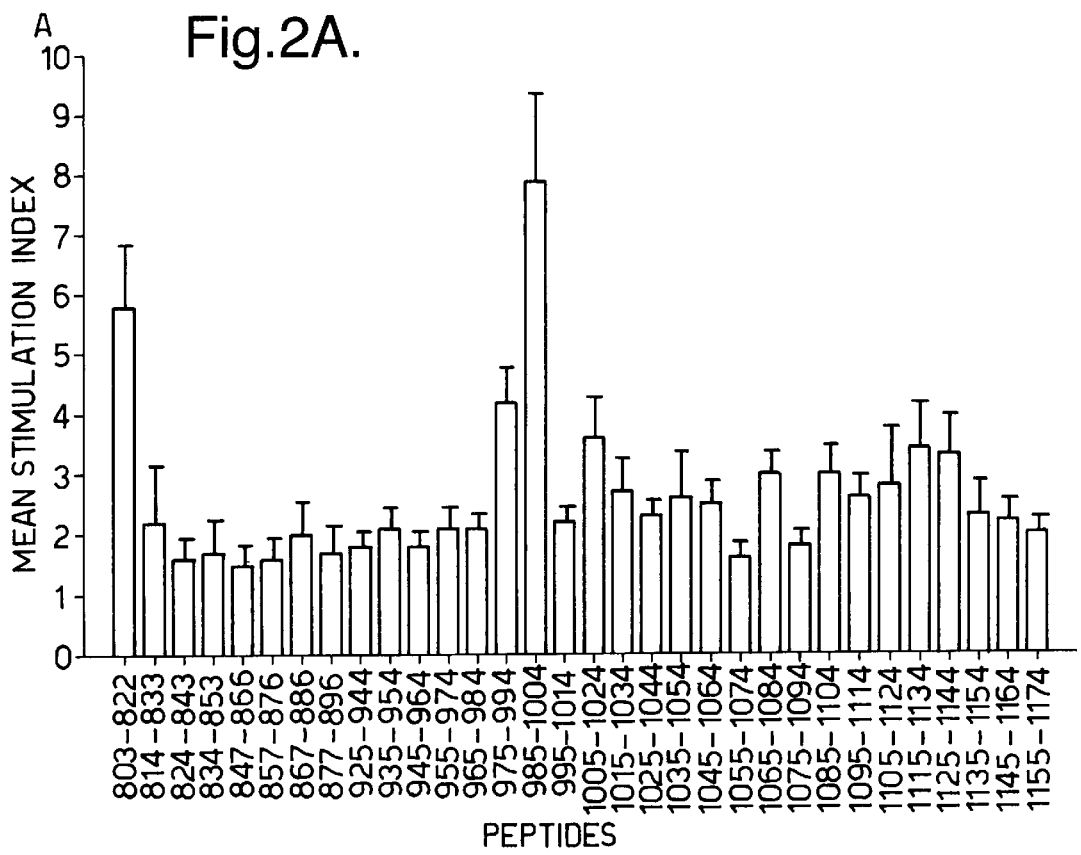
FIGS. 2A and 2B. Proliferative responses to overlapping synthetic peptides ($20^{ers}$) of SA I/II.
Figure 2B:
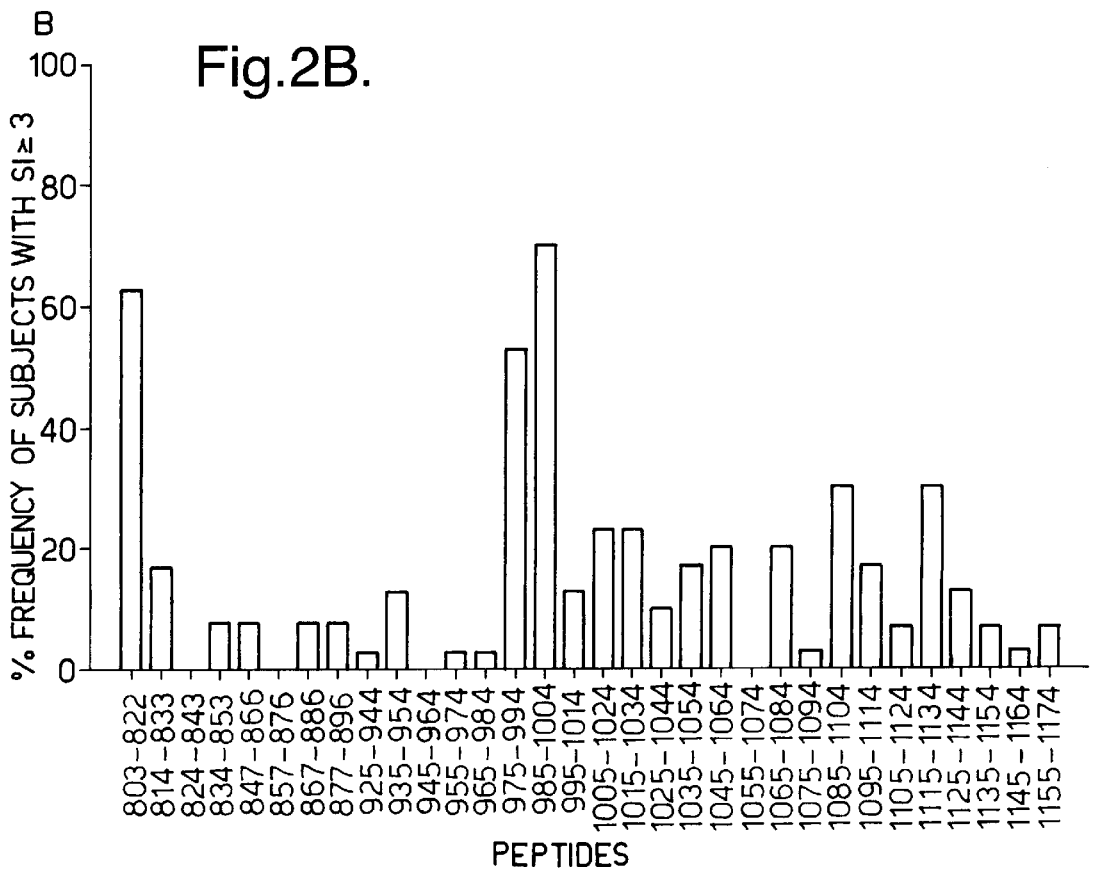

HLA restriction of the T cell response was first studied by dose-dependant inhibition with MAb to HLA class I and II antigen (FIG. 2). The lymphoproliferative response was inhibited by 50% with $\mu$g of MAb to HLA class II (L243) and 10 $\mu$g of the MAb inhibited 100% of the responses (from SI 10.0±3.2 to SI 1.5±0.4). Neither MAb to HLA class I (W6/32) nor the isotype control induced any inhibition of the lymphoproliferative response.

The HLA-DR of 17 subjects were determined and 6 of these were homozygous. The responses of the immunodominant and minor epitopes were then studied in the 6 DR homologous subjects (Table 2). Only peptide 975–994 appeared to be restricted by HLA-DR1. The other 6 peptides stimulated lymphocytes from HLA-DR1, 2 (except AA 1085–1104) and DR6 (except AA 803–822). DR5 was restricted by peptide 803–922, though the latter stimulated lymphocytes with DR1, 2 and 3 antigens. Lymphocytes with DR3 or 4 antigen responded to 3 or 4 peptides. The results suggest that except for peptide 975–994, the remaining 6 peptides appear to be promiscuous as they stimulated lymphocytes with 3 to 5 HLA-DR antigens.

TABLE 1

| DR | 803–822 | 975–994 | 985–1004 | 1005–1024 | 1014–1034 | 1085–1104 | 1115–1134 |
|---|---|---|---|---|---|---|---|
| 1 | 4.1 ± 1.0 | 4.0 ± 1.3 | 5.8 ± 1.8 | 3.2 ± 0.6 | 3.3 ± 1.1 | 3.3 ± 1.3 | 3.2 ± 0.6 |
| 2 | 19.3 ± 6.6 | 2.2 ± 0.4 | 16.7 ± 1.7 | 14.6 ± 5.7 | 11.2 ± 5.2 | 0.6 ± 0.3 | 14.7 ± 3.3 |
| 3 | 6.1 ± 2.7 | 0.7 ± 0.2 | 4.1 ± 2.3 | 1.0 ± 0.2 | 2.1 ± 1.7 | 4.3 ± 1.2 | 1.9 ± 2.3 |
| 4 | 2.5 ± 0.8 | 1.8 ± 0.7 | 3.0 ± 0.3 | 3.2 ± 0.5 | 1.6 ± 0.1 | 3.7 ± 0.6 | 1.5 ± 0.7 |
| 5 | 6.8 ± 1.0 | 1.8 ± 1.3 | 2.0 ± 0.8 | 2.3 ± 0.5 | 1.3 ± 0.3 | 1.2 ± 0.4 | 2.9 ± 2.8 |
| 6 | 2.6 ± 1.5 | 2.9 ± 0.9 | 3.5 ± 0.5 | 8.3 ± 3.1 | 5.7 ± 2.4 | 5.6 ± 1.4 | 5.0 ± 2.0 |

The relationship between HLA-DR1-6 and the T cell responses to 7 synthetic peptides.
S.I (±sem) values of subjects homozygous for DR are shown.
Positive responses (S.I. > 3.0, c.p.m. > 500) are in bold.

Figure 4:
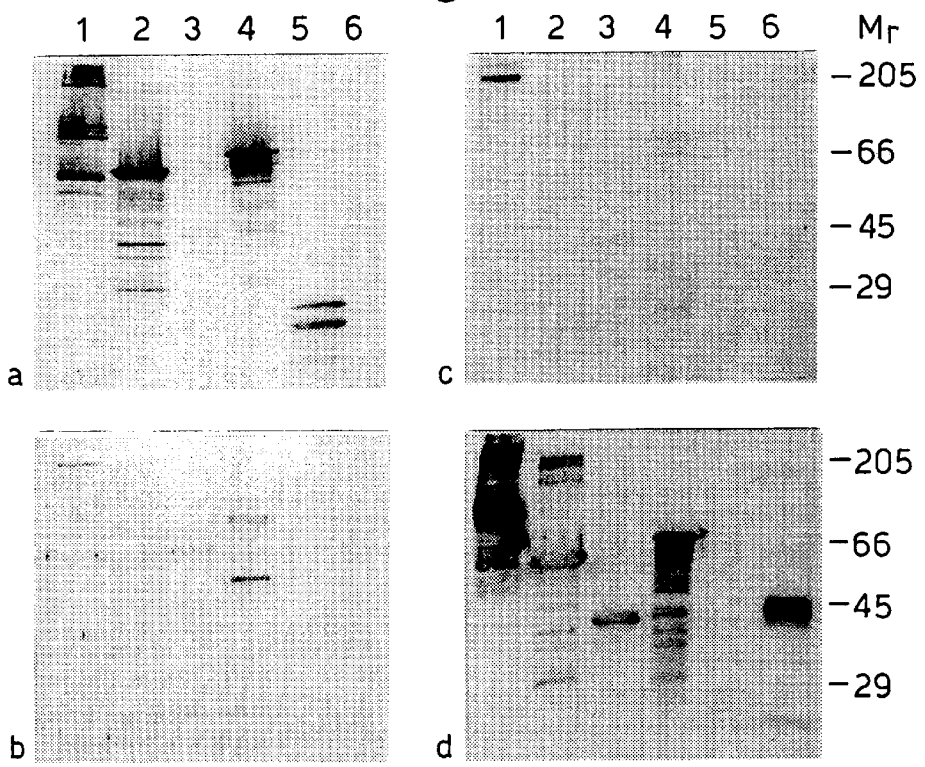
FIGS. 4A–4D. Serum recognition of SA I/II and recombinant polypeptide fragments. Western blots from 3 subjects are shown in FIGS. 4A–4C together with rabbit anti-SA I/II antiserum as shown in FIG. 4D. Lanes, 1, SA I/II; lane 5, recombinant 984–1161.

B Cell Epitope Mapping (see FIG. 4)

Figure 5:
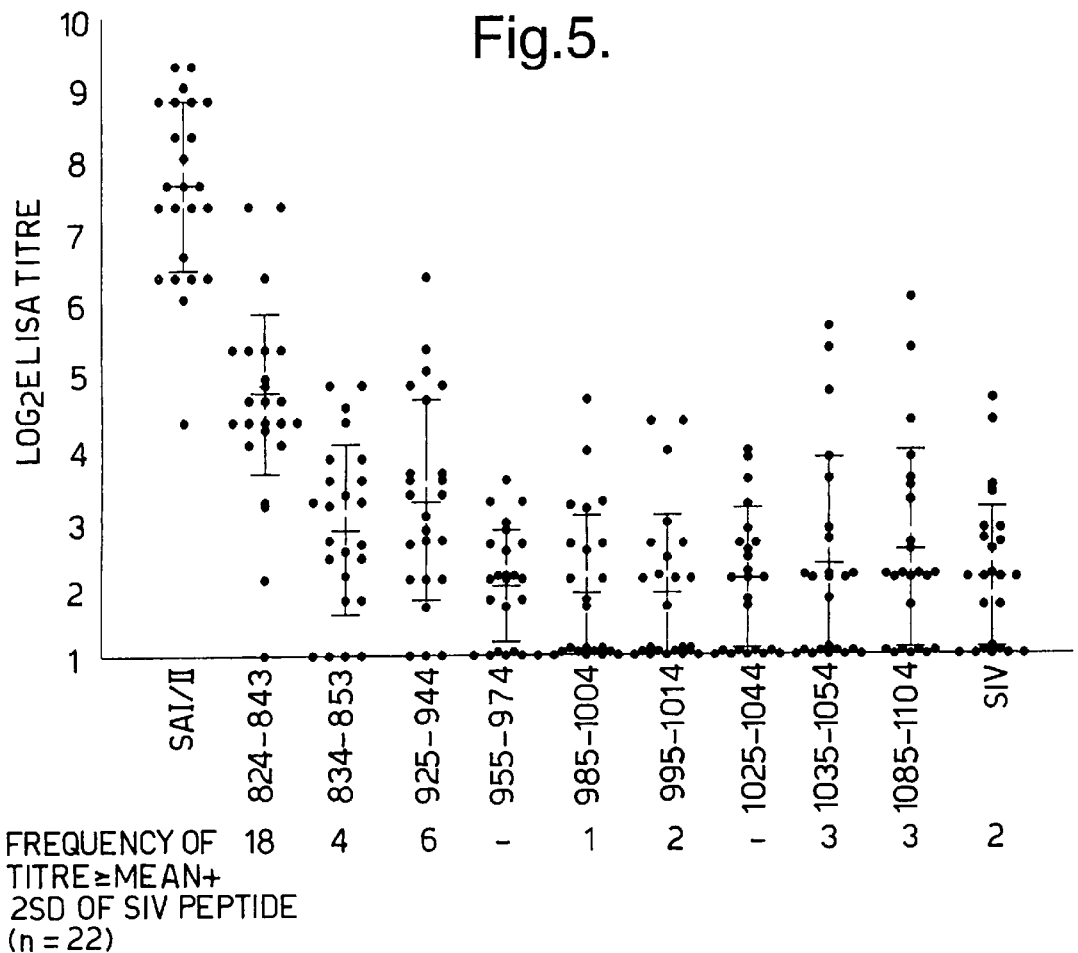
FIG. 5. Human serum recognition of synthetic peptides of SA I/II. Titres were determined by ELISA in 22 subjects to selected peptides of SA I/II and an irrelevant control peptide from SIVp27(SIV). The frequencies of sera binding the peptides with a titre>mean±2S.D. the control peptide are also indicated.

Recognition of the recombinant fragments was assessed by Western blotting. Representative blots obtained with sera from 3 individuals are shown it FIG. 3 together with a positive control using rabbit anti-SA I/II antiserum. In panel a, SA I/II, and 984–1161 were recognised strongly. Rabbit anti-SA I/II antiserum used as a positive control (panel d) recognised recombinant 984–1161. The recombinant polypeptide corresponding to residues 984–1161 was also analysed. SA I/II was recognised by all subjects. B cell epitopes were mapped by ELISA using the panel of synthetic peptides. The panel of peptides was screened with sera from 22 individuals and 8 peptides which were recognised by more than one individual, together with one peptide which was not recognised, were selected for further analyses (FIG. 5). SA I/II was recognised by all subjects with mean $\log_2$ titre of 7.6±1.2. Titres against peptides were lower, with only that against peptide 824–843 (mean $\log_2$ titre 4.7±1.1) being significantly greater than the titre against the control SIV p27 peptide (t=7.28 p<0.01). The proportion of significant titres (>mean+2 standard derivations) was also calculated (FIG. 5) and only peptide 824–843 showed high frequency (18/22). Indeed, an immunodominant B cell epitope is present within peptide 824–843, possibly shared with the overlapping peptide 834–353, while peptides 925–944, 1035–1054 and 1085–1104 constitute minor B cell epitopes. Despite the high frequency of responses to the recombinant polypeptide 984–1161 described above), a very low frequency of responses was observed to peptides within this region.

Saliva samples from the subjects were cultured to determine levels of S. mutans. In 66% of individuals S. mutans was detected (range $10^3$–$10^5$ colony forming units/ml). There was no correlation between S. mutans levels and recognition of particular epitopes or titre against SA I/II.

Adhesion Epitope Mapping

Adherence of S. mutans to saliva-coated microtitre wells (a model of the tooth surface) was determined with [$^3$H]-thymidine labelled S. mutans. The proportion of adhering bacteria was in the range 1–5%. In the absence of saliva, the proportion of adhering bacteria was <0.1%.

Figure 6A:
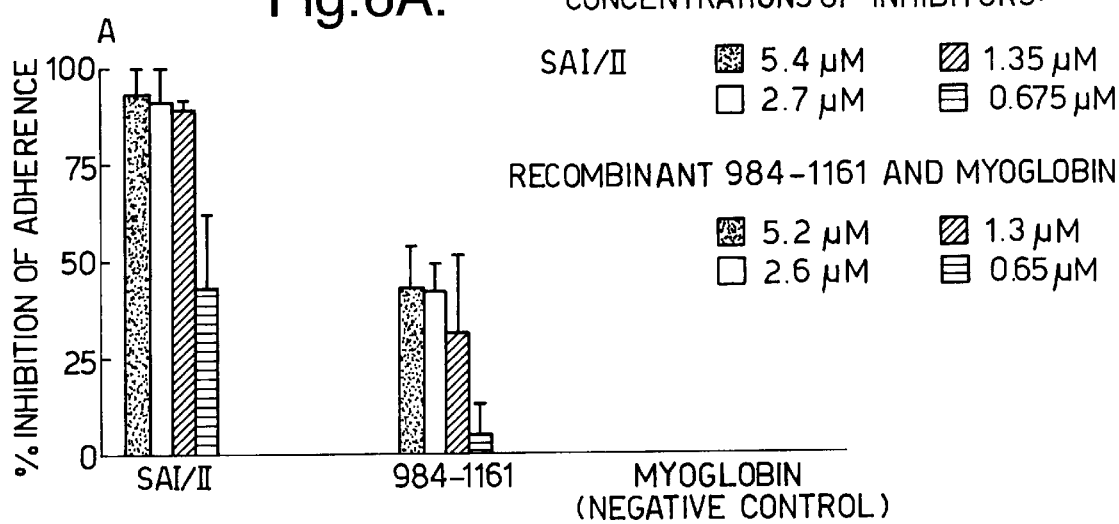
FIGS. 6A and 6B. Inhibition of adhesion of *S. mutans*.
Figure 6B:
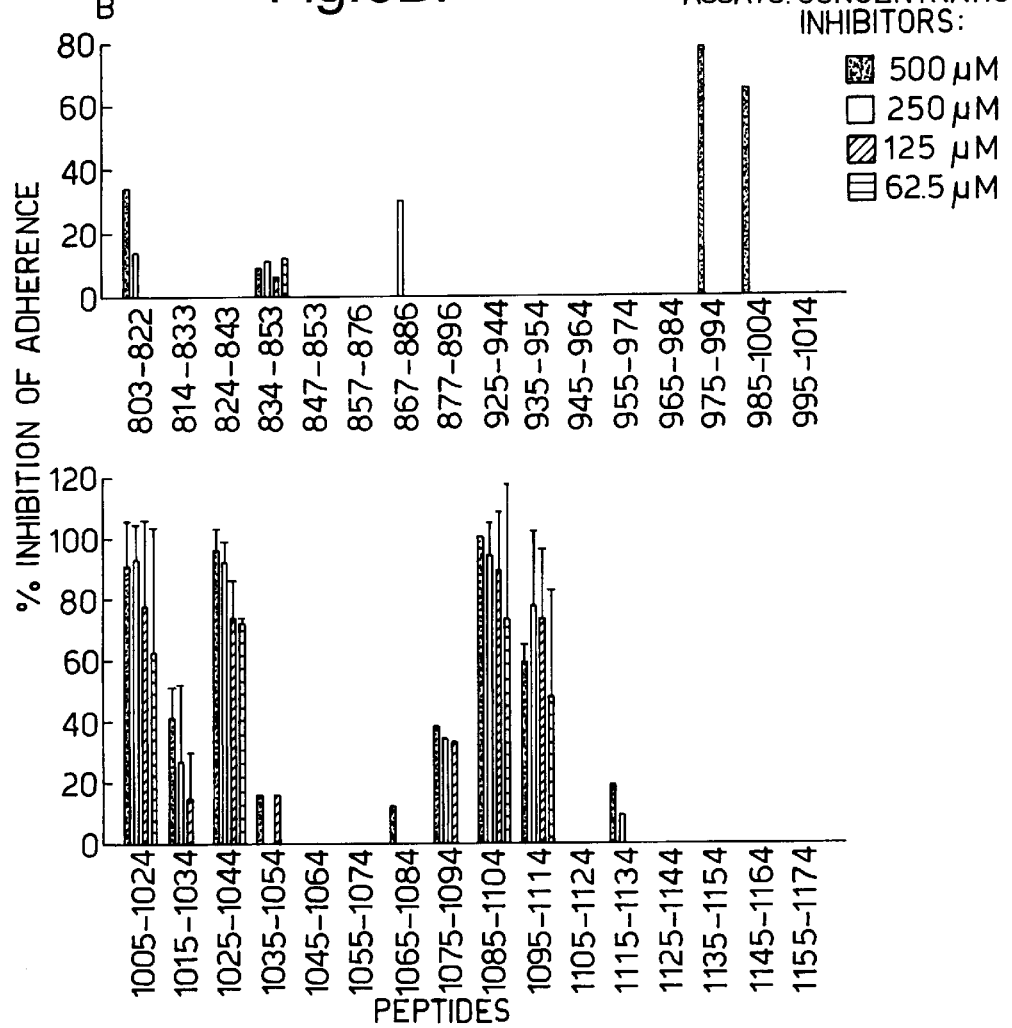

In a series of competitive inhibition assays, the panel of synthetic peptides was assayed for inhibition of adhesion of S. mutans to saliva-coated microtitre wells. Peptides 1005–1024, 1025–1044 and 1085–1104 consistently inhibited adhesion with maximal inhibition ≥90% at concentrations of 500 μM (FIG. 6). Adjacent peptides 1015–1034 and 1095–1114 showed more variable and lower inhibition, and may be part of the adhesion epitopes.

Example 2

Construction of an Expression Vector and Expression of a Recombinant Polypeptide of the Invention (SEQ. ID. No. 8)

Using the oligonucleotide primers TAT CAT ATG CAA GAT CTT CCA ACA CCT CCA TCT ATA (5') (SEQ. ID. NO. 29) and GTC GAC TCA TAC CAA GAC AAA GGA AGT TGT (3') (SEQ. ID. No.30) the portion of the SA I/II gene encoding residues 975–1044 (SEQ. ID. No.8) was amplified by polymerase chain reaction. The amplified gene fragment (with introduced Nde I and Sal I restriction enzyme sites) was cloned using the Ta cloning system and was subcloned into the plasmid pET15b. The recombinant polypeptide was expressed in E. coli BL21 (DE3).

Example 3

Stimulation of an in vitro T-cell Response by the Recombinant Polypeptide (SEQ. ID. No. 8)

Peripheral blood lymphocytes from human volunteers were prepared as described above. Cells were incubated with purified recombinant polypeptide 975–1044 at concentrations of 40, 10 and 1 μg/ml. Cells were also incubated with a protein fraction prepared in the same way from E. coli harbouring non-recombinant plasmid. Proliferative responses of 17 subjects were determined. Mean stimulation index (±sem) was 11.6±2.3 compared with 2.4±0.3 for the control. The frequency of subjects responding (i.e. those with stimulation index≧control+2SD) was 15/17.

Example 4

Immunisation of Mice with the Recombinant Polypeptide (SEQ. ID. NO. 8) (See FIG. 7)

i) Groups of mice (3–4 per group) were immunised with 975–1044 (SEQ. ID. No. 8) by two routes:
a) intraperitoneally with 50 μg polypeptide in incomplete Freund's adjuvant with a boost after 4 weeks (also 50 μg in incomplete Freund's adjuvant and intraperitoneally).
b) subcutaneously. A single immunisation with 50 μg polypeptide in incomplete Freund's adjuvant.
ii) Draining lymph nodes were removed 10 to 14 days after immunisation, pooled and homogenised to give a single cell suspension in RPMI 1640 culture medium supplemented with 2 mM glutamine, 1 mM pyruvate, 50 mM 2-mercaptoethanol, 100 u/ml penicillin, 100 μg/ml streptomycin, 100 mM HEPES and 5% foetal calf serum. Cells ($2 \times 10^5$/well) were cultured with antigen and proliferation was measured by incorporation of [$^3$H]-thymidine as described above. Antigens were SA I/II recombinant polypeptides, peptides spanning residues 975–1044 and a control protein fraction from *E. coli* harbouring non-recombinant plasmid.

Figure 7:
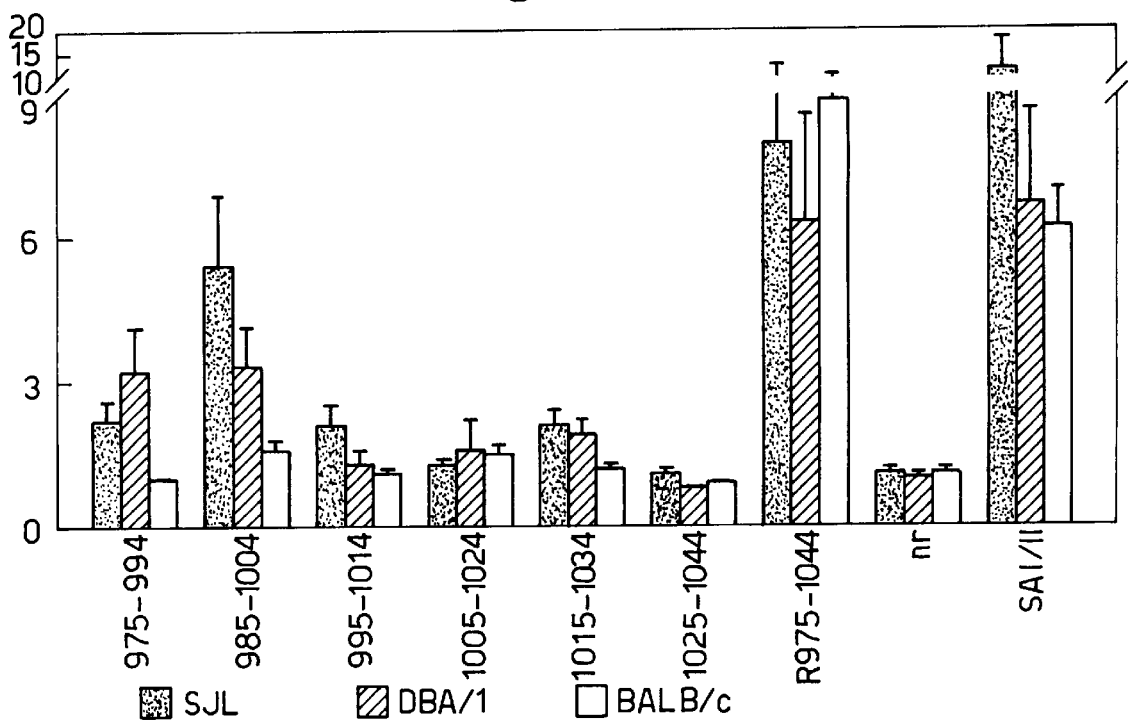
FIG. 7. Proliferative responses of murine splenocytes following immunization with recombinant 975–1044 (SEQ. ID. No. 8)

As in FIG. 7, all mouse strains responded to SA I/II and the recombinant polypeptide 975–1044 (SEQ. ID. No. 8). Positive responses to peptides were those of stimulation index $\geq 3.0$ (cpm>500). SJL mice responded to peptide 985–1004 and DBA/a mice responded to peptide 975–995 and 985–1004. For BALB/c mice, no significant responses to peptides were observed although the response to peptide 985–1004 was greater than responses to the remaining peptides.

iii) Antibody Recognition (See Table 2)

Sera from mice immunised intraperitoneally with polypeptide 975–1044 recognised intact cells of *S.mutans*, intact SA I/II and recombinant 975–1044. Peptides 995–1014 and 1025–1044 were also recognised. The titre for each strain was as in Table 2, which shows log$_2$ titres where initial dilution was 1 in 50 (titre=1).

Binding Analyses

Purified SA I/II or salivary receptor was immobilised on the sensor chip surface at a concentration of 100 µg/ml in 10 mM Na formate pH 3.5 using the amine coupling kit (Pharmacia Biosensor).

i. Inhibition Studies

Binding of immobilised SA I/II to receptors in whole saliva was determined in the absence and presence of inhibitors (at varying concentrations). Inhibition by alanine-substituted peptides was analysed at a peptide concentration of 50 µM. The running buffer was HEPES buffered saline (HBS) and the surface was regenerated with 100 mM HCl.

ii. Direct Binding

Purified salivary receptor was immobilised on the sensor chip and binding of SA I/II or purified recombinant polypeptide fragments was determined.

Results i. Calcium Dependency

In separate determinations with whole saliva, binding to immobilised SA I/II varied from approximately 250 resonance units (RU)—800 RU. In the presence of EDTA,

TABLE 2

Antibody recognition of *S. mutans*, SA I/II and peptides.

| | ANTIGEN | | | | PEPTIDES | | | | |
|---|---|---|---|---|---|---|---|---|---|---|
| STRAIN | S. mutans | SA I/II | 975–1044 | NR Control | 975–994 | 985–1004 | 995–1014 | 995–1014 | 1015–1034 | 1025–1044 |
| SJL | 4.0 | 4.0 | 10.3 | — | — | — | 8.7 | 1.0 | — | 5.7 |
| DBA/1 | 3.0 | 2.7 | 10.7 | — | 0.7 | 0.7 | 4.7 | .2.0 | — | 7.3 |
| BALB/C | 2.0 | 2.8 | 10.7 | — | — | — | 5.7 | 3.0 | — | 4.7 |

Numbers in the table are log$_2$ titres (1 = 1:50)

Example 5

Analysis of the Interaction Between Streptococcal Antigen I/II and Salivary Receptor Using BIAcore Aims In this study, we have used surface plasmon resonance (spr) to analyse the interaction between purified SA I/II and whole human saliva or purified salivary receptor. In addition we have investigated the calcium dependence of binding, identified individual amino acid residues which may be involved in binding and determined the affinity of the interaction between SA I/II and salivary receptor.

Methods

Materials

SA I/II and recombinant polypeptides were prepared as described above. Salivary receptor was prepared by absorption of whole saliva with intact cells of *S. mutans* (Lee et al (1989) Infect. Immun. 57:3306–3313). The cells were washed with KPBS (2.7 mM KCl, 137 mM NaCl in 1.5 mM KH$_2$PO$_4$, 6.5 mM Na$_2$HPO$_4$, pH 7.2) and adsorbed material was eluted with 1 mM EDTA in KPBS. Analysis of the purified material by polyacrylamide gel electrophoresis in the presence of Na dodecyl sulphate indicated the presence of components of Mr>200,000 and approximately 40,000. Peptides were prepared by the simultaneous multiple peptide synthesis procedure (Houghten (1985) Proc. Natl. Acad. Sci. USA 82:5131–5135) as above. In addition, a series of peptides was synthesised corresponding to residues 1025–1044 in which each residue in turn was substituted by alanine.

binding was inhibited with maximal inhibition of 95% at a concentration of 10 mM EDTA. Subsequent binding assays were performed in the presence of 5 mM calcium.

ii. Inhibition of Binding

Figure 8:
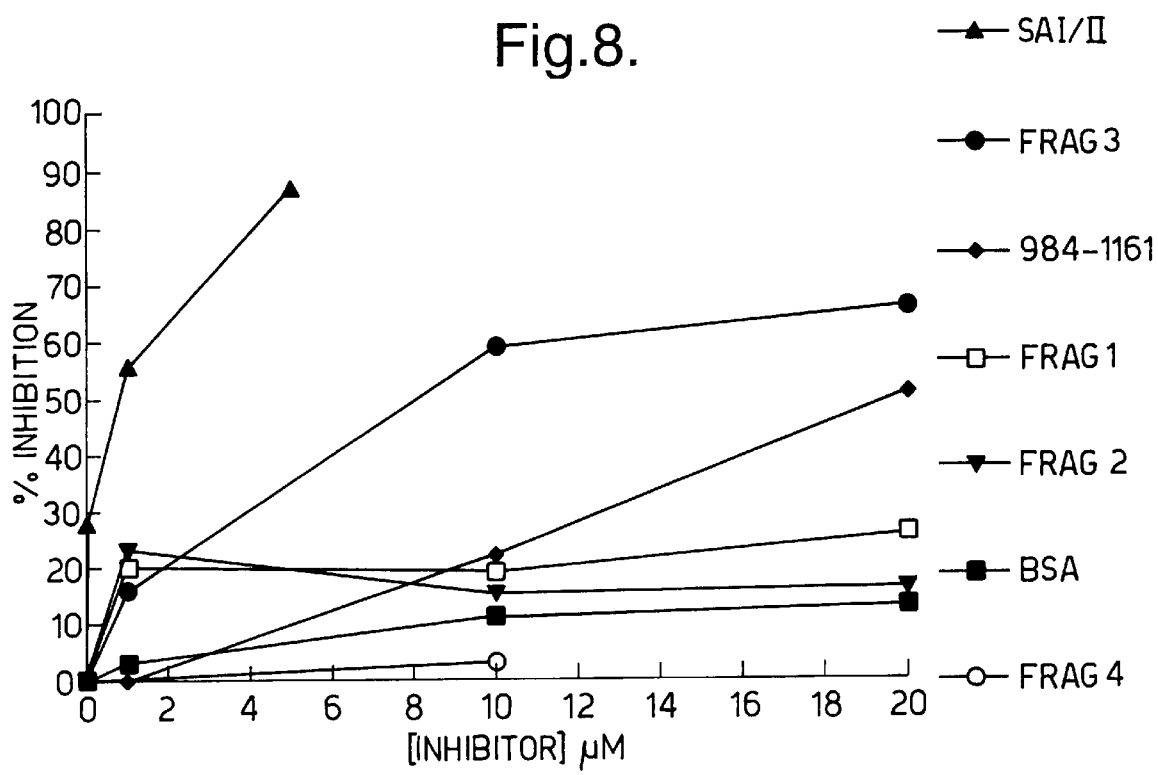
FIG. 8. Competitive inhibition of SA I/II binding by various polypeptides.

Purified SA I/II or recombinant polypeptide fragments 1 (residues 39–481), 2 (residues 475–824), 3 (residues 816–1213), 4 (residues 1155–1538) and recombinant 984–1161 were added to fluid phase saliva as competitive inhibitors at concentrations varying from 0–20 µM. SA I/II inhibited binding most efficiently with approximately 90% inhibition at a concentration of 6 µM (FIG. 8). Of the recombinant fragments, only fragment 3 and r984–1161 inhibited binding to salivary receptors to a significantly greater extent than the control (bovine serum albumin) with maximal inhibition of 65% and 50%, respectively (FIG. 8).

Figure 9:
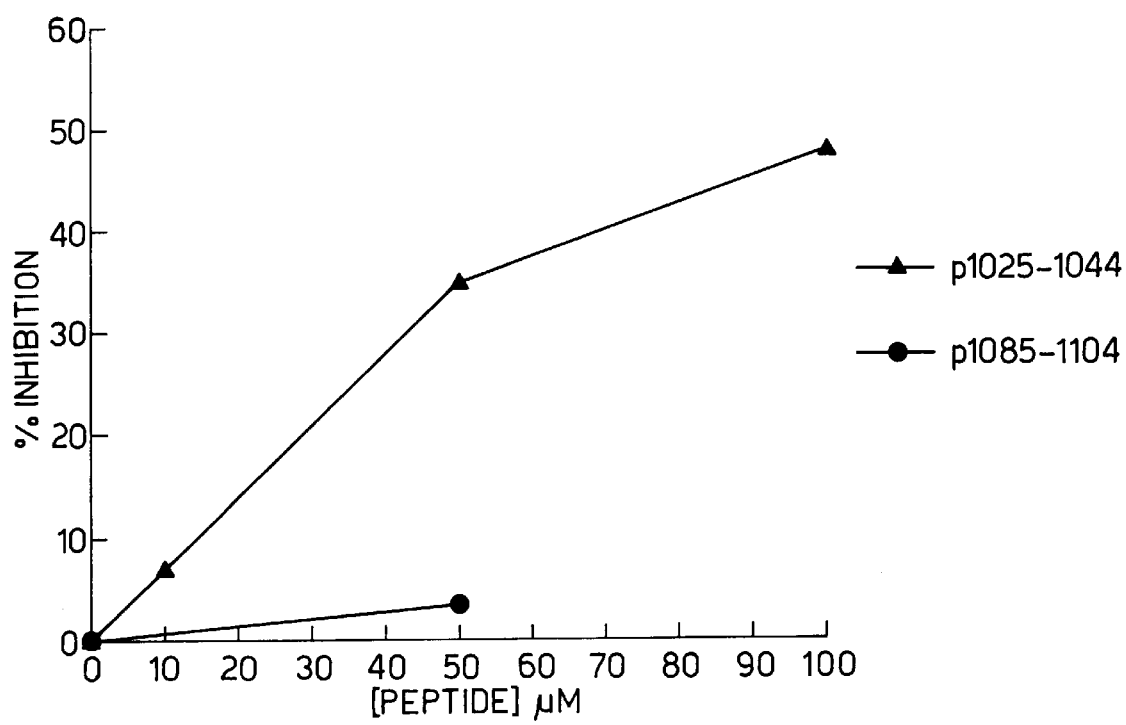
FIG. 9. Dependence of competitive inhibition of SA I/II binding on concentration of two peptides.
Figure 10:
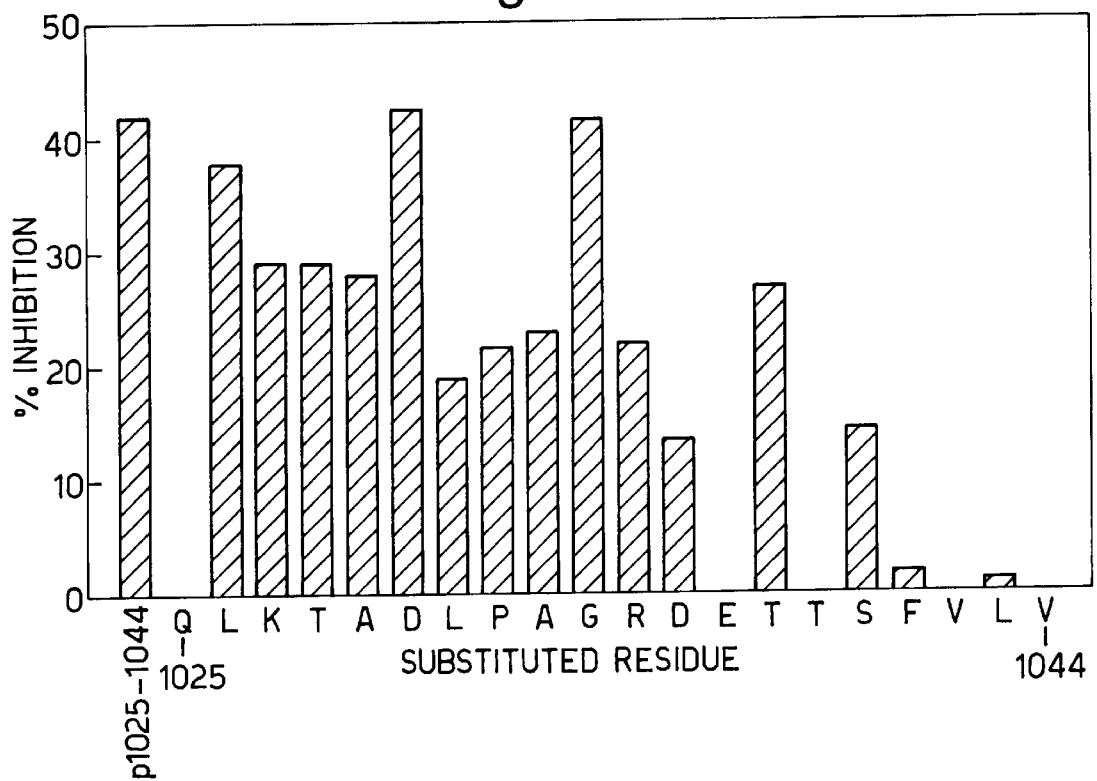
FIG. 10. Effects of substitution of certain residues on competitive inhibition.

A panel of synthetic peptides (20 mers overlapping by 10) spanning residues 803–1174 was assayed for inhibitory activity. Peptide 1025–1044 was the most effective inhibitor although 10–20 fold higher concentrations were required than for polypeptides (FIG. 9). A panel of peptides in which each of the residues 1025–1044 in turn were substituted with alanine (alanine was substituted by serine where it occurred naturally) was also analysed for inhibitory activity. Substitution of Glu (1037) consistently abolished inhibition mediated by the peptide (FIG. 10). Similarly, substitution of Gln 1025, Thr 1039, Phe 1041, Val 1042, Leu 1043 and Val 1044 reduced the inhibition of binding which was mediated by the peptide 1025–1044.

iii. Direct Binding

Figure 11:
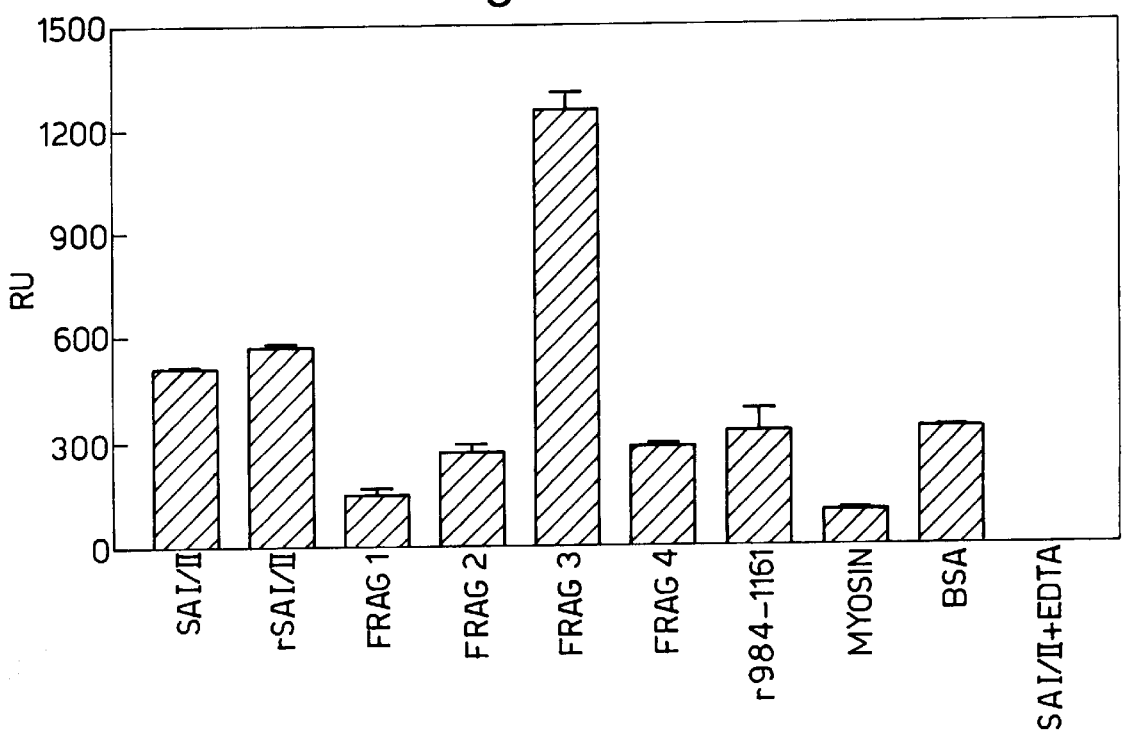
FIG. 11. Comparison of various recombinant polypeptides with respect to binding.

For these analyses, purified salivary receptor was immobilised on the sensor chip and binding to fluid phase SA I/II or recombinant polypeptides was determined. At a concentration of approximately 5 μM both SA I/II and recombinant SA I/II bound to salivary receptor in the range 500–600 RU (FIG. 11). Binding of recombinant polypeptides was determined at a concentration of approximately 20 μM and highest binding was obtained with fragment 3 (1256 RU) (FIG. 11). Binding of other fragments although significantly greater than the myosin control was not greater than the bovine serum albumin control and thus does not appear to be specific. Addition of EDTA (10 μM) in this assay completely inhibited binding of fluid phase SA I/II.

Affinity and rate constants for the adhesin-receptor interaction were determined for SA I/II, recombinant SA I/II and fragment 3 (Table 3). The values indicate a low affinity interaction with a slow association rate constant and a relatively rapid dissociation constant.

Conclusions

These analyses confirm that residues 816–1213 of SA I/II form an adhesion binding region and that within this region, peptide 1025–1044 forms an adhesion epitope. We have now extended these findings by identifying specific residues which may be essential for binding to salivary receptor, namely residues 1025, 1037, 1039 and 1041–1045. The binding is EDTA sensitive and, under the assay conditions, is of relatively low affinity.

TABLE 3

|  |  | SA I/II | recomb. SA I/II | FRAG 3 |
|---|---|---|---|---|
| $k_a$ | $(M^{-1} s^{-1})$ | n.d. | $20.9 \times 10^3$ | $1.5 \times 10^3$ |
| $k_d$ | $(s^{-1})$ | $2 \times 10^{-2}$ | $4.2 \times 10^{-3}$ | $8.1 \times 10^{-3}$ |
| $K_A$ | $(M^{-1})$ | n.d. | $5.0 \times 10^6$ | $0.2 \times 10^6$ | n.d. not determined

---

SEQUENCE INFORMATION

As a result of the experiments detailed above, the following sequences have been identified as being of particular interest.

(i)  Residues 925 to 1114 (SEQ. ID. No. 1). This sequence comprises sequences (iv) and (v) below and includes 2 series of overlapping T-cell, B-cell and adhesion epitopes, a further B-cell epitope, a further T-cell epitope and an adhesion site.

SEQ. ID. No. 1:

TEKPLEPAPVEPSYEAEPTPPTPTPDQPEPNKPVEPTYEVIPTPPTDPVYQDLPTPPSI

PTVHFHYFKLAVQPQVNKEIRNNNDVNIDRTLVAKQSVVKFQLKTADLPAGRDETTSFV

LVDPLPSGYQFNPEATKAASPGFDVAYDNATNTVTFKATAATLATFNADLTKSVATIYP

TVVGQVLNDGATY

Its DNA sequence is (SEQ. ID. No. 12):

ACAGAAAAGCCGTTGGAGCCAGCACCTGTTGAGCCAAGCTATGAAGCAGAGCCAACGCCA

CCGACACCAACACCAGATCAACCAGAACCAAACAAACCTGTTGAGCCAACTTATGAGGTT

ATTCCAACACCGCCGACTGATCCTGTTTATCAAGATCTTCCAACACCTCCATCTATACCA

ACTGTTCATTTCCATTACTTTAAACTAGCTGTTCAGCCGCAGGTTAACAAAGAAATTAGA

AACAATAACGATGTTAATATTGACAGAACTTTGGTGGCTAAACAATCTGTTGTTAAGTTC

CAGCTGAAGACAGCAGATCTCCCTGCTGGACGTGATGAAACAACTTCCTTTGTCTTGGTA

GATCCCCTGCCATCTGGTTATCAATTTAATCCTGAAGCTACAAAAGCTGCCAGCCCTGGC

TTTGATGTCGCTTATGATAATGCAACTAATACAGTCACCTTCAAGGCAACTGCAGCAACT

TTGGCTACGTTTAATGCTGATTTGACTAAGTCAGTGGCAACGATTTATCCAACAGTGGTC

GGACAAGTTCTTAATGATGGCGCAACTTAT (ii)  Residues 1005 to 1044 (SEQ. ID. No. 2). This comprises a T-cell epitope overlapping two adhesion sites.

SEQ. ID. No. 2

-continued

SEQUENCE INFORMATION

NNNDVNIDRTLVAKQSVVKFQLKTADLPAGRDETTSFVLV

Its DNA sequence is (SEQ. ID. No. 13)

AACAATAACGATGTTAATATTGACAGAACTTTGGTGGCTAAACAATCTGTTGTTAAGTTC

CAGCTGAAGACAGCAGATCTCCCTGCTGGACGTGATGAAACAACTTCCTTTGTCTTGGTA (iii) Residues 1085–1104 (SEQ. ID. No. 3). Here, a T-cell epitope, a B-cell epitope and an adhesion site overlap.

SEQ. ID. No. 3:

LATFNADLTKSVATIYPTVV

Its DNA sequence is (SEQ. ID. No. 14)

TTGGCTACGTTTAATGCTGATTTGACTAAGTCAGTGGCAACGATTTATCCAACAGTGGTC (iv) Residues 1005 to 1114 (SEQ. ID. No. 4). This comprises sequences (ii) and (iii) above and therefore includes two sequences in which a B-cell epitope a T-cell epitopes and an adhesion site overlap.

SEQ. ID. No. 4

NNNDVNIDRTLVAKQSVVKFQLKTADLPAGRDETTSFVLVDPLPSGYQFNPEATKAASPGF

DVAYDNATNTVTFKATAATLATFNADLTKSVATIYPTVVGQVLNDGATY

Its DNA sequence is (SEQ. ID. No. 15)

AACAATAACGATGTTAATATTGACAGAACTTTGGTGGCTAAACAATCTGTTGTTAAGTTC

CAGCTGAAGACAGCAGATCTCCCTGCTGGACGTGATGAAACAACTTCCTTTGTCTTGGTA

GATCCCCTGCCATCTGGTTATCAATTTAATCCTGAAGCTACAAAAGCTGCCAGCCCTGGC

TTTGATGTCGCTTATGATAATGCAACTAATACAGTCACCTTCAAGGCAACTGCAGCAACT

TTGGCTACGTTTAATGCTGATTTGACTAAGTCAGTGGCAACGATTTATCCAACAGTGGTC

GGACAAGTTCTTAATGATGGCGCAACTTAT (v) Residues 925 to 1004 (SEQ. ID. No. 5). This comprises a B-cell epitope, an immunodominant T-cell epitope and an adhesion site.

SEQ. ID. No. 5:

TEKPLEPAPVEPSYEAEPTPPTPTPDQPEPNKPVEPTYEVIPTPPTDPVYQDLPTPPSIPT

VHFHYFKLAVQPQVNKEIR

Its DNA sequence is (SEQ. ID. No. 16):

ACAGAAAAGCCGTTGGAGCCAGCACCTGTTGAGCCAAGCTATGAAGCAGAGCCAACGCCA

CCGACACCAACACCAGATCAACCAGAACCAAACAAACCTGTTGAGCCAACTTATGAGGTT

ATTCCAACACCGCCGACTGATCCTGTTTATCAAGATCTTCCAACACCTCCATCTATACCA

ACTGTTCATTTCCATTACTTTAAACTAGCTGTTCAGCCGCAGGTTAACAAAGAAATTAGA

-continued

SEQUENCE INFORMATION (vi) Residues 925 to 1054 (SEQ. ID. No. 6). This comprises sequence (v) above, together with a further adjacent adhesion site and a further overlapping B-cell epitope.

SEQ. ID. No. 6

TEKPLEPAPVEPSYEAEPTPPTPTPDQPEPNKPVEPTYEVIPTPPTDPVYQDLPTPPSIPT

VHFHYFKLAVQPQVNKEIRNNNDVNIDRTLVAKQSVVKFQLKTADLPAGRDETTSFVLVDP

LPSGYQFN

Its DNA sequence is (SEQ. ID. No. 17):

ACAGAAAAGCCGTTGGAGCCAGCACCTGTTGAGCCAAGCTATGAAGCAGAGCCAACGCCA

CCGACACCAACACCAGATCAACCAGAACCAAACAAACCTGTTGAGCCAACTTATGAGGTT

ATTCCAACACCGCCGACTGATCCTGTTTATCAAGATCTTCCAACACCTCCATCTATACCA

ACTGTTCATTTCCATTACTTTAAACTAGCTGTTCAGCCGCAGGTTAACAAAGAAATTAGA

AACAATAACGATGTTAATATTGACAGAACTTTGGTGGCTAAACAATCTGTTGTTAAGTTC

CAGCTGAAGACAGCAGATCTCCCTGCTGGACGTGATGAAACAACTTCCTTTGTCTTGGTA

GATCCCCTGCCATCTGGTTATCAATTTAAT (vii) Residues 803-854 (SEQ. ID. No. 7). This comprises a major T-cell epitope and adjacent immunodominant B-cell epitope.

SEQ. ID. No. 7:

ETGKKPNIWYSLNGKIRAVNLPKVTKEKPTPPVKPTAPTKPTYETEKPLKPA

Its DNA sequence is (SEQ. ID. No. 18)

GAAACCGGCAAAAAACCAAATATTTGGTATTCATTAAATGGTAAAATCCGTGCGGTTAAT

CTTCCTAAAGTTACTAAGGAAAAACCCACACCTCCGGTTAAACCAACAGCTCCAACTAAA

CCAACTTATGAAACAGAAAAGCCATTAAAACCGGCA (viii) Residues 975 to 1044 (SEQ. ID. No. 8). This comprises a T-cell epitope, a B-cell epitope and an adhesion site.

SEQ. ID No. 8:

QDLPTPPSIPTVHFHYFKLAVQPQVNKEIRNNNDVNIDRTLVAKQSVVKFQLKTADLPAGR

DETTSFVLV

Its DNA sequence is (SEQ. ID. No. 19):

CAAGATCTTCCAACACCTCCATCTATACCAACTGTTCATTTCCATTACTTTAAACTAGCT

GTTCAGCCGCAGGTTAACAAAGAAATTAGAAACAATAACGATGTTAATATTGACAGAACT

SEQUENCE INFORMATION

```
TTGGTGGCTAAACAATCTGTTGTTAAGTTCCAGCTGAAGACAGCAGATCTCCCTGCTGGA

CGTGATGAAACAACTTCCTTTGTCTTGGTA
```

(ix) Residues 1024 to 1044 (SEQ. ID. No. 9). This comprises a T-cell epitope overlapping with an adhesion site.

SEQ. ID. No. 9

```
FQLKTADLPAGRDETTSFVLV
```

Its DNA Sequence is (SEQ. ID. No. 20):

```
TTCCAGCTGAAGACAGCAGATCTCCCTGCTGGACGTGATGAAACAACTTCCTTTGTCTTG

GTA
```

(x) Residues 803 to 1114 (SEQ. ID. No. 10). This comprises sequences (i) and (vii) above and some intervening sequence. Residues 803 to 1114 comprise 2 series of overlapping T-cell, B-cell and adhesion epitopes, a further T-cell epitope and a further adhesion site and an immunodominant B-cell epitope and a major T-cell epitope.

SEQ. ID. No. 10:

```
ETGKKPNIWYSLNGKIRAVNLPKVTKEKPTPPVKPTAPTKPTYETEKPLKPAPV

APNYEKEPTPPTRTPDQAEPKKPTPPTYETEKPLEPAPVEPSYEAEPTPPTRTPDQAE

PNKPTPPTYETEKPLEPAPVEPSYEAEPTPPTPTPDQPEPNKPVEPTYEVIPTPPTDP

VYQDLPTPPSIPTVHFHYFKLAVQPQVNKEIRNNNDVNIDRTLVAKQSVVKFQLKTAD

LPAGRDETTSFVLVDPLPSGYQFNPEATKAASPGFDVAYDNATNTVTFKATAATLATF

NADLTKSVATIYPTVVGQVLNDGATY
```

Its DNA Sequence is (SEQ. ID. NO. 21):

```
GAAACCGGCAAAAAACCAAATATTTGGTATTCATTAAATGGTAAAATCCGTGCGGTTAAT

CTTCCTAAAGTTACTAAGGAAAAACCCACACCTCCGGTTAAACCAACAGCTCCAACTAAA

CCAACTTATGAAACAGAAAAGCCATTAAAACCGGCACCAGTAGCTCCAAATTATGAAAAG

GAGCCAACACCACCGACAAGAACACCGGATCAAGCAGAGCCAAAGAAACCCACTCCGCCG

ACCTATGAAACAGAAAAGCCGTTGGAGCCAGCACCTGTTGAGCCAAGCTATGAAGCAGAG

CCAACACCGCCGACAAGGACACCGGATCAGGCAGAGCCAAATAAACCCACACCGCCGACC

TATGAAACAGAAAAGCCGTTGGAGCCAGCACCTGTTGAGCCAAGCTATGAAGCAGAGCCA

ACGCCACCGACACCAACACCAGATCAACCAGAACCAAACAAACCTGTTGAGCCAACTTAT

GAGGTTATTCCAACACCGCCGACTGATCCTGTTTATCAAGATCTTCCAACACCTCCATCT

ATACCAACTGTTCATTTCCATTACTTTAAACTAGCTGTTCAGCCGCAGGTTAACAAAGAA

ATTAGAAACAATAACGATGTTAATATTGACAGAACTTTGGTGGCTAAACAATCTGTTGTT

AAGTTCCAGCTGAAGACAGCAGATCTCCCTGCTGGACGTGATGAAACAACTTCCTTTGTC

TTGGTAGATCCCCTGCCATCTGGTTATCAATTTAATCCTGAAGCTACAAAAGCTGCCAGC

CCTGGCTTTGATGTCGCTTATGATAATGCAACTAATACAGTCACCTTCAAGGCAACTGCA
```

SEQUENCE INFORMATION

GCAACTTTGGCTACGTTTAATGCTGATTTGACTAAGTCAGTGGCAACGATTTATCCAACA

GTGGTCGGACAAGTTCTTAATGATGGCGCAACTTAT (xi) Residues 975 to 1004 (SEQ. ID. No. 11), which comprise a T-cell epitope.

SEQ. ID. No. 11:

QDLPTPPSIPTVHFHYFKLAVQPQVNKEIR

Its DNA Sequence is (SEQ. ID. NO. 22):

CAAGATCTTCCAACACCTCCATCTATACCAACTGTTCATTTCCATTACTTTAAACTAGCT

GTTCAGCCGCAGGTTAACAAAGAAATTAGA

The amino acid sequence of SA I/II is as follows, beginning with residue No. 1 (SEQ ID No. 23).

MKVKKTYGFRKSKISKTLCGAVLGTVAAVSVAGQKVFADETTTT

SDVDTKVVGTQTGNPATNLPEAQGSASKQAEQSQTKLERQMVHTIEVPKTDLDQAAKD

AKSAGVNVVQDADVNKGTVKTAEEAVQKETEIKEDYTKQAEDIKKTTDQYKSDVAAHE

AEVAKIKAKNQATKEQYGKDMVAHKAEVERINAANAASKTAYEAKLAQYQADLAAVQK

TNAANQASYQKALAAYQAELKRVQEANAAAKAAYDTAVAANNAKNTEIAAANEEIRKR

NATAKAEYETKLAQYQAELKRVQEANAANEADYQAKLTAYQTELARVQKANADAKAAY

EAAVAANNAKNAALTAENTAIKQRNENAKATYEAALKQYEADLAAVKKANAANEADYQ

AKLTAYQTELARVQKANADAKAAYEAAVAANNAANAALTAENTAIKKRNADAKADYEA

KLAKYQADLAKYQKDLADYPVKLKAYEDEQASIKAALAELEKHKNEDGNLTEPSAQNL

VYDLEPNANLSLTTDGKFLKASAVDDAFSKSTSKAKYDQKILQLDDLDITNLEQSNDV

ASSMELYGNFGDKAGWSTTVSNNSQVKWGSVLLERGQSATATYTNLQNSYYNGKKISK

IVYKYTVDPKSKFQGQKVWLGIFTDPTLGVFASAYTGQVEKNTSIFIKNEFTFYDEDG

KPINFDNALLSVASLNRENNSIEMAKDYTGKFVKISGSSIGEKNGMIYATDTLNFRQG

QGGARWTMYTRASEPGSGWDSSDAPNSWYGAGAIRMSGPNNSVTLGAISSTLVVPADP

TMAIETGKKPNIWYSLNGKIRAVNLPKVTKEKPTPPVKPTAPTKPTYETEKPLKPAPV

APNYEKEPTPPTRTPDQAEPKKPTPPTYETEKPLEPAPVEPSYEAEPTPPTRTPDQAE

PNKPTPPTYETEKPLEPAPVEPSYEAEPTPPTPTPDQPEPNKPVEPTYEVIPTPPTDP

VYQDLPTPPSIPTVHFHYFKLAVQPQVNKEIRNNNDVNIDRTLVAKQSVVKFQLKTAD

LPAGRDETTSFVLVDPLPSGYQFNPEATKAASPGFDVAYDNATNTVTFKATAATLATF

NADLTKSVATIYPTVVGQVLNDGATYKNNFSLTVNDAYGIKSNVVRVTTPGKPNDPDN

PNNNYIKPTKVNKNENGVVIDGKTVLAGSTNYYELTWDLDQYKNDRSSADTIQQGFYY

VDDYPEEALELRQDLVKITDANGNEVTGVSVDNYTSLEAAPQEIRDVLSKAGIRPKGA

FQIFRADNPREFYDTYVKTGIDLKIVSPMVVKKQMGQTGGSYEDQAYQIDFGNGYASN

IVINNVPKINPKKDVTLTLDPADTNNVDGQTIPLNTVFNYRLIGGIIPANHSEELFEY

NFYDDYDQTGDHYTGQYKVFAKVDITLKNGVIIKSGTELTQYTTAEVDTTKGAITIKF

KEAFLRSVSIDSAFQAESYIQMKRIAVGTFENTYINTVNGVTYSSNTVKTTTPEDPAD

PTDPQDPSSPRTSTVIIYKPQSTAYQPSSVQKTLPNTGVTNNAYMPLLGIIGLVTSFSL

SEQUENCE INFORMATION

LGLKAKKD

Its DNA sequence is as follows (SEQ ID No. 24):

```
   1 ATTTCAGCAA AAATTGACAA ATCAAATCAA TTATATTACA ATTTTTTAAC
  51 GTATATTACA AAAATATATT TGGAAGATTT ATTCAGATTT GGAGGATTTA
 101 TGAAAGTCAA AAAAACTTAC GGTTTTCGTA AAAGTAAAAT TAGTAAAACA
 151 CTGTGTGGTG CTGTTCTAGG AACAGTAGCA GCAGTCTCTG TAGCAGGACA
 201 AAAGGTTTTT GCCGATGAAA CGACCACTAC TAGTGATGTA GATACTAAAG
 251 TAGTTGGAAC ACAAACTGGA ATCCAGCGA CCAATTTGCC AGAGGCTCAA
 301 GGAAGTGCGA GTAAGCAAGC TGAACAAAGT CAAACCAAGC TGGAGAGACA
 351 AATGGTTCAT ACCATTGAAG TACCTAAAAC TGATCTTGAT CAAGCAGCAA
 401 AAGATGCTAA GTCTGCTGGT GTCAATGTTG TCCAAGATGC CGATGTTAAT
 451 AAAGGAACTG TTAAAACAGC TGAAGAAGCA GTCCAAAAAG AAACTGAAAT
 501 TAAAGAAGAT TACACAAAAC AAGCTGAGGA TATTAAGAAG ACAACAGATC
 551 AATATAAATC GGATGTAGCT GCTCATGAGG CAGAAGTTGC TAAAATCAAA
 601 GCTAAAAATC AGGCAACTAA AGAACAGTAT GGAAAAGATA TGGTAGCTCA
 651 TAAAGCCGAG GTTGAACGCA TTAATGCTGC AAATGCTGCC AGTAAAACAG
 701 CTTATGAAGC TAAATTGGCT CAATATCAAG CAGATTTAGC AGCCGTTCAA
 751 AAAACCAATG CTGCCAATCA AGCATCCTAT CAAAAAGCCC TTGCTGCTTA
 801 TCAGGCTGAA CTGAAACGTG TTCAGGAAGC TAATGCAGCC GCCAAAGCCG
 851 CTTATGATAC TGCTGTAGCA GCAAATAATG CCAAAAATAC AGAAATTGCC
 901 GCTGCCAATG AAGAAATTAG AAAACGCAAT GCAACGGCCA AAGCTGAATA
 951 TGAGACTAAG TTAGCTCAAT ATCAAGCTGA ACTAAAGCGT GTTCAGGAAG
1001 CTAATGCCGC AAACGAAGCA GACTATCAAG CTAAATTGAC CGCCTATCAA
1051 ACAGAGCTTG CTCGCGTTCA GAAAGCCAAT GCAGATGCTA AGCGGCCTA
1101 TGAAGCAGCT GTAGCAGCAA ATAATGCCAA AAATGCGGCA CTTACAGCTG
1151 AAAATACTGC AATTAAGCAA CGCAATGAGA ATGCTAAGGC GACTTATGAA
1201 GCTGCACTCA AGCAATATGA GGCTGATTTG CAGCGGTGA AAAAAGCTAA
1251 TGCCGCAAAC GAAGCAGACT ATCAAGCTAA ATTGACCGCC TATCAAACAG
1301 AGCTCGCTCG CGTTCAAAAG GCCAATGCGG ATGCTAAAGC GGCCTATGAA
1351 GCAGCTGTAG CAGCAAATAA TGCCGCAAAT GCAGCGCTCA CAGCTGAAAA
1401 TACTGCAATT AAGAAGCGCA ATGCGGATGC TAAAGCTGAT TACGAAGCAA
1451 AACTTGCTAA GTATCAAGCA GATCTTGCCA AATATCAAAA AGATTTAGCA
1501 GACTATCCAG TTAAGTTAAA GGCATACGAA GATGAACAAG CTTCTATTAA
1551 AGCTGCACTG GCAGAACTTG AAAAACATAA AAATGAAGAC GGAAACTTAA
1601 CAGAACCATC TGCTCAAAAT TTGGTCTATG ATCTTGAGCC AAATGCGAAC
1651 TTATCTTTGA CAACAGATGG GAAGTTCCTT AAGGCTTCTG CTGTGGATGA
1701 TGCTTTTAGC AAAAGCACTT CAAAAGCAAA ATATGACCAA AAAATTCTTC
1751 AATTAGATGA TCTAGATATC ACTAACTTAG AACAATCTAA TGATGTTGCT
```

-continued

| SEQUENCE INFORMATION |
|---|

```
1801 TCTTCTATGG AGCTTTATGG CAATTTTGGT GATAAAGCTG GCTGGTCAAC
1851 GACAGTAAGC AATAACTCAC AGGTTAAATG GGGATCGGTA CTTTTAGAGC
1901 GCGGTCAAAG CGCAACAGCT ACATACACTA ACCTGCAGAA TTCTTATTAC
2001 GTCCAAGTTT CAAGGTCAAA AGGTTTGGTT AGGTATTTTT ACCGATCCAA
1951 AATGGTAAAA AGATTTCTAA AATTGTCTAC AAGTATACAG TGGACCCTAA
2051 CTTTAGGTGT TTTTGCTTCC GCTTATACAG GTCAAGTTGA AAAAAACACT
2101 TCTATTTTTA TTAAAAATGA ATTCACTTTC TATGACGAAG ATGGAAAACC
2151 AATTAATTTT GATAATGCCC TTCTATCAGT AGCTTCTCTT AACCGAGAAA
2201 ATAATTCTAT TGAGATGGCC AAAGATTATA CGGGTAAATT TGTCAAAATC
2251 TCTGGATCAT CTATCGGTGA AAAGAATGGC ATGATTTATG CTACAGATAC
2301 TCTCAACTTT AGGCAGGGTC AAGGTGGTGC TCGTTGGACC ATGTATACCA
2351 GAGCTAGCGA ACCGGGATCT GGCTGGGATA GTTCAGATGC GCCTAACTCT
2401 TGGTATGGTG CTGGTGCTAT CCGCATGTCT GGTCCTAATA ACAGTGTGAC
2451 TTTGGGTGCT ATCTCATCAA CACTTGTTGT GCCTGCTGAT CCTACAATGG
2501 CAATTGAAAC CGGCAAAAAA CCAAATATTT GGTATTCATT AAATGGTAAA
2551 ATCCGTGCGG TTAATCTTCC TAAAGTTACT AAGGAAAAAC CCACACCTCC
2601 GGTTAAACCA ACAGCTCCAA CTAAACCAAC TTATGAAACA GAAAAGCCAT
2651 TAAAACCGGC ACCAGTAGCT CCAAATTATG AAAAGGAGCC AACACCACCG
2701 ACAAGAACAC CGGATCAAGC AGAGCCAAAG AAACCCACTC CGCCGACCTA
2751 TGAAACAGAA AAGCCGTTGG AGCCAGCACC TGTTGAGCCA AGCTATGAAG
2801 CAGAGCCAAC ACCGCCGACA AGGACACCGG ATCAGGCAGA GCCAAATAAA
2851 CCCACACCGC CGACCTATGA AACAGAAAAG CCGTTGGAGC CAGCACCTGT
2901 TGAGCCAAGC TATGAAGCAG AGCCAACGCC ACCGACACCA ACACCAGATC
2951 AACCAGAACC AAACAAACCT GTTGAGCCAA CTTATGAGGT TATTCCAACA
3001 CCGCCGACTG ATCCTGTTTA TCAAGATCTT CCAACACCTC CATCTATACC
3051 AACTGTTCAT TTCCATTACT TTAAACTAGC TGTTCAGCCG CAGGTTAACA
3101 AAGAAATTAG AAACAATAAC GATGTTAATA TTGACAGAAC TTTGGTGGCT
3151 AAACAATCTG TTGTTAAGTT CCAGCTGAAG ACAGCAGATC TCCCTGCTGG
3201 ACGTGATGAA ACAACTTCCT TTGTCTTGGT AGATCCCCTG CCATCTGGTT
3251 ATCAATTTAA TCCTGAAGCT ACAAAAGCTG CCAGCCCTGG CTTTGATGTC
3301 GCTTATGATA ATGCAACTAA TACAGTCACC TTCAAGGCAA CTGCAGCAAC
3351 TTTGGCTACG TTTAATGCTG ATTTGACTAA GTCAGTGGCA ACGATTTATC
3401 CAACAGTGGT CGGACAAGTT CTTAATGATG GCGCAACTTA TAAGAATAAT
3451 TTCTCGCTCA CAGTCAATGA TGCTTATGGC ATTAAATCCA ATGTTGTTCG
3501 GGTGACAACT CCTGGTAAAC CAAATGATCC AGATAACCCA AATAATAATT
3551 ACATTAAGCC AACTAAGGTT AATAAAAATG AAAATGGCGT TGTTATTGAT
3601 GGTAAAACAG TTCTTGCCGG TTCAACGAAT TATTATGAGC TAACTTGGGA
3651 TTTGGATCAA TATAAAAACG ACCGCTCTTC AGCAGATACC ATTCAACAAG
```

-continued

SEQUENCE INFORMATION

3701 GATTTTACTA TGTAGATGAT TATCCAGAAG AAGCGCTTGA ATTGCGTCAG

3751 GATTTAGTGA AGATTACAGA TGCTAATGGC AATGAAGTTA CTGGTGTTAG

3801 TGTGGATAAT TATACTAGTC TTGAAGCAGC CCCTCAAGAA ATTAGAGATG

3851 TTCTTTCTAA GGCAGGAATT AGACCTAAAG GTGCTTTCCA AATTTTCCGT

3901 GCCGATAATC CAAGAGAATT TTATGATACT TATGTCAAAA CTGGAATTGA

3951 TTTGAAGATT GTATCACCAA TGGTTGTTAA AAAACAAATG GGACAAACAG

4001 GCGGGAGTTA TGAAGATCAA GCTTACCAAA TTGACTTTGG TAATGGTTAT

4051 GCATCAAATA TCGTTATCAA TAATGTTCCT AAGATTAACC CTAAGAAAGA

4101 TGTGACCTTA ACACTTGATC CGGCTGATAC AAATAATGTT GATGGTCAGA

4151 CTATTCCACT TAATACAGTC TTTAATTACC GTTTGATTGG TGGCATTATC

4201 CCTGCAAATC ACTCAGAAGA ACTCTTTGAA TACAATTTCT ATGATGATTA

4251 TGATCAAACA GGAGATCACT ATACTGGTCA GTATAAAGTT TTTGCCAAGG

4301 TTGATATCAC TCTTAAAAAC GGTGTTATTA TCAAGTCAGG TACTGAGTTA

4351 ACTCAGTATA CGACAGCGGA AGTTGATACC ACTAAAGGTG CTATCACAAT

4401 TAAGTTCAAG GAAGCCTTTC TGCGTTCTGT TTCAATTGAT TCAGCCTTCC

4451 AAGCTGAAAG TTATATCCAA ATGAAACGTA TTGCGGTTGG TACTTTTGAA

4501 AATACCTATA TTAATACTGT CAATGGGGTA ACTTACAGTT CAAATACAGT

4551 GAAAACAACT ACTCCTGAGG ATCCTGCAGA CCCTACTGAT CCGCAAGATC

4601 CATCATCACC GCGGACTTCA ACTGTAATTA TCTACAAACC TCAATCAACT

4651 GCTTATCAAC CAAGCTCTGT CCAAAAAACG TTACCAAATA CGGGAGTAAC

4701 AAACAATGCT TATATGCCTT TACTTGGTAT TATTGGCTTA CTTACTAGTT

4751 TTAGTTTGCT TGGCTTAAAG GCTAAGAAAG ATTGACAGCA TAGATATTAC

4801 ATTAGAATTA AAAAGTGAGA TGAAGCGATA AATCACAGAT TGAGCTTTTA

4851 TCTCATTTTT TGATT

We claim:

1. A polypeptide or an extended polypeptide, wherein said extended polypeptide is extended at the N-terminus or C-terminus or both with non-wild-type amino acid sequence to form said extended polypeptide;

wherein said polypeptide is selected from the group consisting of a polypeptide consisting of an amino acid sequence corresponding to residues 925–1114 of the *Streptococcus mutans* antigen I/II (SA I/II) (SEQ ID NO: 1);

a polypeptide consisting of an amino acid sequence corresponding to residues 1005–1044 of SA I/II (SEQ ID NO:2);

a polypeptide consisting of an amino acid sequence corresponding to residues 1085–1104 of SA I/II (SEQ ID NO:3);

a polypeptide consisting of an amino acid sequence corresponding to residues 1005–1114 of SA I/II (SEQ ID NO:4);

a polypeptide consisting of an amino acid sequence corresponding to residues 925–1004 of SA I/II (SEQ ID NO:5);

a polypeptide consisting of an amino acid sequence corresponding to residues 925–1054 of SA I/II (SEQ ID NO:6);

a polypeptide consisting of an amino acid sequence corresponding to residues 803–854 of SA I/II (SEQ ID NO:7);

a polypeptide consisting of an amino acid sequence corresponding to residues 975–1044 of SA I/II (SEQ ID NO:8);

a polypeptide consisting of an amino acid sequence corresponding to residues 1024–1044 of SA I/II (SEQ ID NO:9);

a polypeptide consisting of an amino acid sequence corresponding to residues 1025–1044 of SA I/II (residues 2–21 of SEQ ID NO:9);

a polypeptide consisting of an amino acid sequence corresponding to residues 804–1114 of SA I/II (SEQ ID NO:10);

a polypeptide consisting of an amino acid sequence corresponding to residues 975–1004 of SA I/II (SEQ ID NO:11); and a polypeptide which differs from any of the aforesaid polypeptides by up to and including 8 amino acid alterations wherein said alterations consist of the substitution and/or deletion and/or insertion of up to and including 8 amino acids and having the same immunological and adhesion properties as said corresponding sequence of any one of the aforesaid polypeptides; and wherein said polypeptide or extended polypeptide may be in the N-terminal acylated and/or C-terminal amidated form.

2. The polypeptide or extended polypeptide of claim 1 which has the amino acid sequence corresponding to SEQ ID NO:9 or differs from said sequence by up to and including 8 amino acid alterations wherein said alterations consist of substitution and/or insertion and/or deletion of 1, 2, 3, 4, 5 or 8 amino acids.

3. The polypeptide or extended polypeptide of claim 2 wherein said polypeptide has the amino acid sequence of SEQ ID NO:9 or differs from said amino acid sequence of SEQ ID NO:9 by virtue of substitution, deletion or insertion of one amino acid.

4. A pharmaceutical composition comprising the polypeptide or extended polypeptide of claim 1 in a pharmaceutically acceptable carrier.

5. A pharmaceutical composition comprising the polypeptide or extended polypeptide of claim 3 in a pharmaceutically acceptable carrier.

6. An immunological composition comprising the polypeptide or extended polypeptide of claim 1 along with an immunologically acceptable carrier.

7. An immunological composition comprising the polypeptide or extended polypeptide of claim 3 along with an immunologically acceptable carrier.

8. The composition of claim 4 which is formulated for topical application in the mouth.

9. The composition of claim 5 which is formulated for topical application in the mouth.

10. A method to vaccinate or treat a mammalian host against dental caries which method comprises administering to the host an effective amount of the polypeptide or extended polypeptide of claim 1.

11. A method to vaccinate or treat a mammalian host against dental caries which method comprises administering to the host an effective amount of the polypeptide or extended polypeptide of claim 3.

12. The method of claim 10 wherein the polypeptide or extended polypeptide is administered by topical application in the mouth.

13. The method of claim 11 wherein the polypeptide or extended polypeptide is administered by topical application in the mouth.

14. The polypeptide or extended polypeptide of claim 1 wherein said polypeptide consists of the amino acid sequence corresponding to residues 1025–1044 of SA I/II (residues 2–21 of SEQ ID NO:9).

15. A pharmaceutical composition comprising the polypeptide or extended polypeptide of claim 14 in a pharmaceutically acceptable carrier.

16. An immunological composition comprising the polypeptide or extended polypeptide of claim 14 along with an immunologically acceptable carrier.

17. The composition of claim 15 which is formulated for topical application in the mouth.

18. A method to vaccinate or treat a mammalian host against dental caries which method comprises administering to the host an effective amount of the polypeptide or extended polypeptide of claim 14.

19. The method of claim 18 wherein the polypeptide or extended polypeptide is administered by topical application in the mouth.

20. The polypeptide or extended polypeptide of claim 1 wherein said polypeptide is selected from the group consisting of a polypeptide consisting of an amino acid sequence corresponding to residues 925–1114 of the *Streptococcus mutans* antigen I/II (SA I/II) (SEQ ID NO:1);

a polypeptide consisting of an amino acid sequence corresponding to residues 1005–1044 of SA I/II (SEQ ID NO:2);

a polypeptide consisting of an amino acid sequence corresponding to residues 1085–1104 of SA I/II (SEQ ID NO:3);

a polypeptide consisting of an amino acid sequence corresponding to residues 1005–1114 of SA I/II (SEQ ID NO:4);

a polypeptide consisting of an amino acid sequence corresponding to residues 925–1004 of SA I/II (SEQ ID NO:5);

a polypeptide consisting of an amino acid sequence corresponding to residues 925–1054 of SA I/II (SEQ ID NO:6);

a polypeptide consisting of an amino acid sequence corresponding to residues 803–854 of SA I/II (SEQ ID NO:7);

a polypeptide consisting of an amino acid sequence corresponding to residues 975–1044 of SA I/II (SEQ ID NO:8);

a polypeptide consisting of an amino acid sequence corresponding to residues 1024–1044 of SA I/II (SEQ ID NO:9);

a polypeptide consisting of an amino acid sequence corresponding to residues 1025–1044 of SA I/II (residues 2–21 of SEQ ID NO:9);

a polypeptide consisting of an amino acid sequence corresponding to residues 804–1114 of SA I/II (SEQ ID NO:10); and a polypeptide consisting of an amino acid sequence corresponding to residues 975–1004 of SA I/II (SEQ ID NO:11).

21. The polypeptide or extended polypeptide of claim 20 wherein said polypeptide is selected from the group consisting of a polypeptide consisting of an amino acid sequence corresponding to residues 1005–1044 of the *Streptococcus mutans* antigen I/II (SA I/II) (SEQ ID NO:2);

a polypeptide consisting of an amino acid sequence corresponding to residues 1085–1104 of SA I/II (SEQ ID NO:3);

a polypeptide consisting of an amino acid sequence corresponding to residues 1005–1114 of SA I/II (SEQ ID NO:4);

a polypeptide consisting of an amino acid sequence corresponding to residues 925–1004 of SA I/II (SEQ ID NO:5);

a polypeptide consisting of an amino acid sequence corresponding to residues 925–1054 of SA I/II (SEQ ID NO:6);

a polypeptide consisting of an amino acid sequence corresponding to residues 803–854 of SA I/II (SEQ ID NO:7);

a polypeptide consisting of an amino acid sequence corresponding to residues 975–1044 of SA I/II (SEQ ID NO:8);

a polypeptide consisting of an amino acid sequence corresponding to residues 1024–1044 of SA I/II (SEQ ID NO:9);

a polypeptide consisting of an amino acid sequence corresponding to residues 1025–1044 of SA I/II (residues 2–21 of SEQ ID NO:9); and a polypeptide consisting of an amino acid sequence corresponding to residues 975–1004 of SA I/II (SEQ ID NO:11).

22. A pharmaceutical composition comprising the polypeptide or extended polypeptide of claim 20 in a pharmaceutically acceptable carrier.

23. A pharmaceutical composition comprising the polypeptide or extended polypeptide of claim 21 in a pharmaceutically acceptable carrier.

24. A method to vaccinate or treat a mammalian host against dental caries which method comprises administering to the host an effective amount of the polypeptide or extended polypeptide of claim 20.

25. A method to vaccinate or treat a mammalian host against dental caries which method comprises administering to the host an effective amount of the polypeptide or extended polypeptide of claim 21.

26. The method of claim 24 wherein the polypeptide or extended polypeptide is administered by topical application in the mouth.

27. The method of claim 25 wherein the polypeptide or extended polypeptide is administered by topical application in the mouth.

28. An immunological composition comprising the polypeptide or extended polypeptide of claim 20 along with an immunologically acceptable carrier.

29. An immunological composition comprising the polypeptide or extended polypeptide of claim 21 along with an immunologically acceptable carrier.

30. The composition of claim 22 which is formulated for topical application in the mouth.

31. The composition of claim 23 which is formulated for topical application in the mouth.

* * * * *